(12) United States Patent
Fan et al.

(10) Patent No.: US 11,572,371 B2
(45) Date of Patent: Feb. 7, 2023

(54) BRD4 INHIBITOR

(71) Applicant: HINOVA PHARMACEUTICALS INC., Sichuan (CN)

(72) Inventors: Lei Fan, Sichuan (CN); Kexin Xu, Sichuan (CN); Ke Chen, Sichuan (CN); Fei Wang, Sichuan (CN); Xiaoquan Wu, Sichuan (CN); Tongchuan Luo, Sichuan (CN); Shaohua Zhang, Sichuan (CN); Xinghai Li, Sichuan (CN); Yuanwei Chen, Sichuan (CN)

(73) Assignee: HINOVA PHARMACEUTICALS INC., Sichuan (CN)

( * ) Notice: Subject to any disclaimer, the term of this patent is extended or adjusted under 35 U.S.C. 154(b) by 177 days.

(21) Appl. No.: 16/647,837

(22) PCT Filed: Sep. 14, 2018

(86) PCT No.: PCT/CN2018/105620
§ 371 (c)(1),
(2) Date: Mar. 16, 2020

(87) PCT Pub. No.: WO2019/052519
PCT Pub. Date: Mar. 21, 2019

(65) Prior Publication Data
US 2020/0255450 A1 Aug. 13, 2020

(30) Foreign Application Priority Data

Sep. 14, 2017 (CN) .......................... 201710828398.1

(51) Int. Cl.
C07D 495/14 (2006.01)
A61P 35/00 (2006.01)
(52) U.S. Cl.
CPC ............ *C07D 495/14* (2013.01); *A61P 35/00* (2018.01)
(58) Field of Classification Search
CPC ..... C07D 495/14; C07D 495/04; A61P 35/00; A61P 17/00; A61P 29/00; A61P 31/00; A61P 31/14; A61P 31/20; A61P 31/22; A61P 37/00; A61P 1/00; A61P 1/16; A61P 3/10; A61P 11/00; A61P 11/02; A61P 11/06; A61P 17/06; A61P 19/02; A61P 21/04; A61P 25/28; A61P 31/18; A61P 37/06; A61P 37/08; A61P 31/12; A61K 31/551
USPC .................................................... 514/210.18
See application file for complete search history.

(56) References Cited

U.S. PATENT DOCUMENTS

2015/0376196 A1* 12/2015 Schmees ................ A61P 13/08
514/210.18

FOREIGN PATENT DOCUMENTS

| CN | 103037865 A | 4/2013 |
| EP | 0638560 A1 | 2/1995 |
| WO | 2015018520 A1 | 2/2015 |
| WO | 2017027571 A1 | 2/2017 |
| WO | 2018144789 A1 | 8/2018 |

OTHER PUBLICATIONS

Junichi, Endo et al.; "A phenotypic drug discovery study on thienodiazepine derivatives as inhibitors of T cell proliferation induced by CD28 co-stimulation leads to the discovery of a first bromodomain inhibitor"; Bioorganic & Medicinal Chemistry Letters; vol. 26, Issue 5, Mar. 1, 2016, pp. 1365-1370.
Wang, Le et al.; "Fragment-Based, Structure-Enabled Discovery of Novel Pyridones and Pyridone Macrocycles as Potent Bromodomain and Extra-Terminal Domain (BET) Family Bromodomain Inhibitors"; Apr. 3, 2017, Journal of Medicinal Chemical, vol. 60, Issue 9, pp. 3828-3850.
Tyler, Dean S. et al.; "Click chemistry enables preclinical evaluation of targeted epigenetic therapies"; Science vol. 356, Issue 6345, pp. 1397-1401, Jul. 30, 2017.
Moon, Kyoo Jang et al.; "The Bromodomain Protein Brd4 Is a Positive Regulatory Component of P-TEFb and Stimulates RNA Polymerase II-Dependent Transcription"; Molecular Cell, vol. 19, Aug. 18, 2005, pp. 523-534.
Devaiah, Ballachanda N. et al.; "BRD4 is an atypical kinase that phosphorylates Serine2 of the RNA Polymerase II carboxy-terminal domain"; Science, May 1, 2012 vol. 109, No. 18, 6927-6932.
Ni, Ping et al., "A preliminary study of BRD4 inhibitor JQ1 effects on non-small cell lung cancer cells", Acta Universitatis Medicinalis Nanjing (Natural Science), Aug. 2015, vol. 35, No. 8.

* cited by examiner

*Primary Examiner* — Taylor V Oh
(74) *Attorney, Agent, or Firm* — Novick, Kim & Lee, PLLC; Allen Xue

(57) ABSTRACT

Disclosed is a BRD4 inhibitor as shown in formula I, belonging to the field of compound drugs. The compound provided has a good inhibitory effect on prostate cancer cell proliferation, and can be used for preparing a drug combatting tumors, autoimmune or inflammatory diseases and viral infection, and in particular an anti-prostate cancer drug.

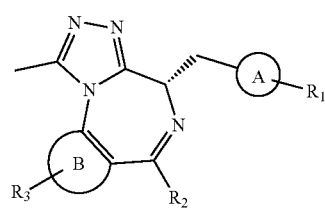

15 Claims, No Drawings

BRD4 INHIBITOR

TECHNICAL FIELD

The present invention belongs to the field of compound medicine, and particularly relates to a BRD4 inhibitor.

BACKGROUND ART

The BRD4 protein in the bromodomain of BET family contains acetylated lysine residues capable of binding histones and other proteins, and plays a key role in the regulation of gene transcription and the control of cell growth. The BRD4 protein is involved in the regulation of large protein complexes related with the transcription of many genes, including mediators, PAFc, and superelongation complexes. The investigation done by Jang et al. (Mol. Cell, 2005, 19, 523-534) indicates that the kinase activity of BRD4 can directly phosphorylate and activate RNA polymerase II, thereby regulating the transcriptional expression of genes. Devaiah et al., Rroc. Nat. Acad. Sci., USA 2012, 109, 6927-6932 report that the progression of cells lacking BRD4 through the cell cycle is influenced. The investigation has shown that many human diseases are closely related to BRD4 protein, such as tumors and bacterial inflammation. For example, in the models of hematopoietic tumors including lymphoma, multiple myeloma, and B-cell acute lymphocytic leukemia, the expression of MYC can be inhibited by interfering with the binding of BRD4 to the oncogene MYC.

BRD4 is inhibited by the inhibitors targeting it. BRD4 inhibitors have great values in anti-cancer and anti-inflammatory as well as many other fields, and has attracted close attention from major pharmaceutical companies and scientific research institutions. For example, Dr. Hernando found that BRD4 was over-expressed in melanoma cells and maintained tumor cell proliferation in 2013. When its expression was suppressed, the growth rate of tumor cells is significantly retarded. Chen Chong, entitled "The effect and possible mechanism of BRD4 inhibitor GSK525762A on the proliferation and apoptosis of acute B lymphocytic leukemia cells", the National Symposium on the Progress of Lymphoma Diagnosis and Treatment, 2014, shows that BRD4 inhibitors can inhibit the proliferation of acute B lymphocytic leukemia cells and promote their apoptosis. Ni Ping, et al., entitled "A preliminary study of BRD4 inhibitor JQ1 effects on non-small cell lung cancer cells", Journal of Nanjing Medical University (Natural Science Edition), 2015, issue 08, show that BRD4 inhibitors can inhibit the growth of non-small cell lung cancer. At present, small molecule compounds that can block the specific binding of lysine acetylate and BRD4 have gradually become a research focus.

CONTENT OF THE INVENTION

The object of the present invention is to provide a kind of BRD4 inhibitors.

A compound of formula (I), or a solvate thereof, or a pharmaceutically acceptable salt thereof:

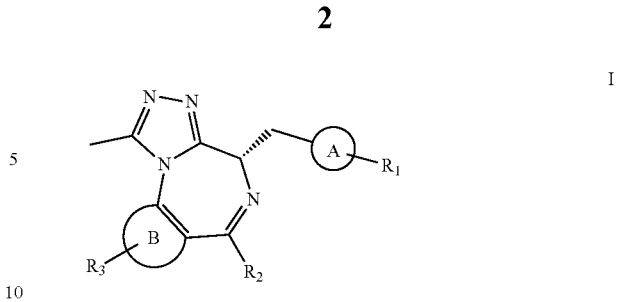

Wherein, ring A represents 5-6 membered aromatic ring or heteroaromatic ring; R1 represents 0-3 substituents in ring A;

$R_1$ is selected from the group consisting of hydrogen, halogen, C1-C8 alkyl, C1-C8 haloalkyl, C1-C8 alkoxy, C3-C8 cycloalkyl, substituted aryl, substituted heteroaryl, C3-C8 heterocycloalkyl, —$(CH_2)_m$O$(CH_2)_n$H, —$(CH_2)_m$CO$(CH_2)_n$H, —$(CH_2)_m$SO$_2$$(CH_2)_n$H, —$(CH_2)_m$CO$_2$$(CH_2)_n$H—$(CH_2)_m$CONH$(CH_2)_n$H —$(CH_2)_m$NH$(CH_2)_n$H, —$(CH_2)_m$SO$_2$NH$(CH_2)_n$H

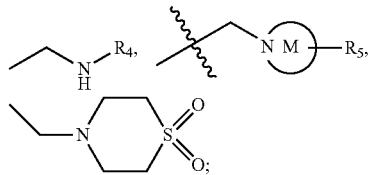

m and n are independently selected from integers of 0-5, respectively;

$R_4$ is selected from H, —C(=O)Ra, —Ra—OH,

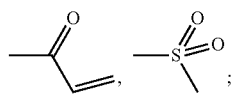

M represents a 3-7 membered ring containing nitrogen atom; $R_5$ represents 0-3 substituents in ring M;

$R_5$ is selected from H, C1-C5 alkyl, hydroxyl, halogen, carboxyl, and

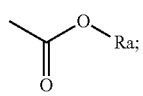

Ra represents C1-C5 alkyl or alkylenyl;

Ring B is 5-6 membered aromatic ring or heteroaromatic ring; ring B, together with the seven-membered heterocycle linkage with it, shares two carbon atoms; $R_3$ represents 0-3 substituents in ring B;

$R_3$ is selected from H, halogen, C1-C8 alkyl and cycloalkyl, and C1-C8 alkoxyl;

$R_2$ represents a benzene ring with 1-3 substituents, and the substituents are selected from halogen, hydroxyl, C1-C5 alkyl, and C1-C5 alkoxyl.

Further, ring B is a five-membered heteroaromatic ring.
Further, ring B is a ring of containing S atom.
Further, ring B has two substituents.
Further, the substituent in ring B is methyl.
Further, $R_2$ is a mono-substituted benzene ring.
Further, $R_2$ is a halogenated benzene.

Further, said compound has a structure of formula (II):

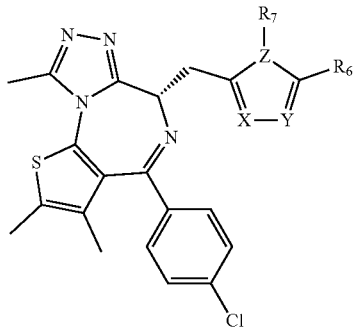

Wherein, X, Y, Z are C or heteroatoms independently;

R₆ is selected from H, C1-C5 alkyl, C3-C5 cycloalkyl, C1-C5 haloalkyl, —(CH₂)ₘO(CH₂)ₙH,

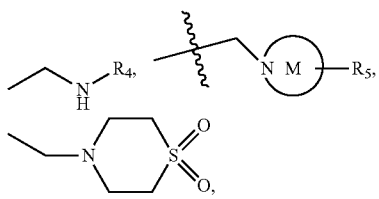

respectively;

m and n are independently selected from integers of 0-5, respectively;

R₄ is selected from H, —C(=O)Ra, —Ra—OH,

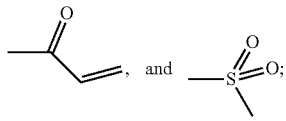

M represents a 3-7 membered ring having nitrogen atom; R₅ represents 0-3 substituents in ring M;

R₅ is selected from H, hydroxyl, carboxyl, and

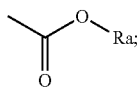

Wherein, Ra represents C1-C5 alkyl or alkylenyl;

R₇ is absent or C1-C5 alkyl, C1-C5 alkoxyl.

Further, X, Y, and Z are independently selected from C, N, or O, respectively.

Further, m and n are independently selected from integers of 0-3, respectively.

Further, R₇ is absent or isopropyl.

Further, M is a 4-6 membered aliphatic ring.

Further, ring M has one N atom.

Further, said compound has structures as follow:

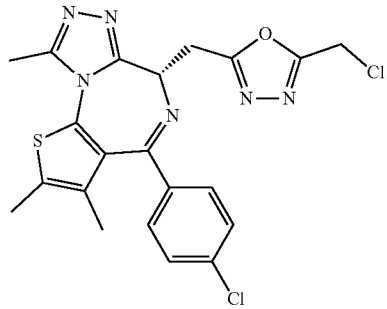

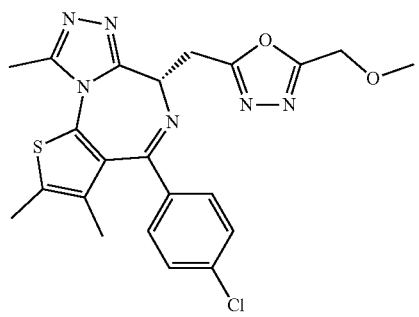

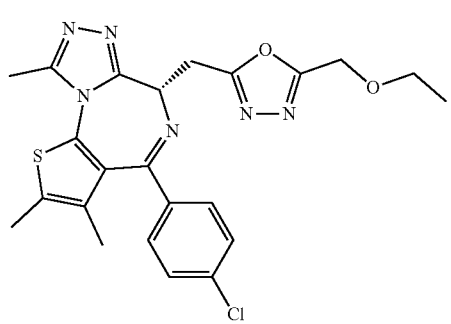

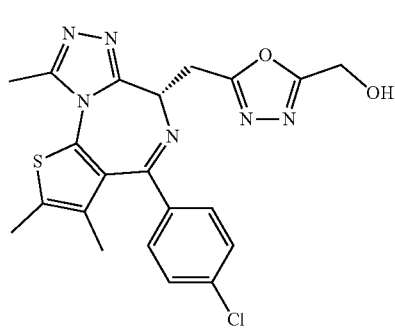

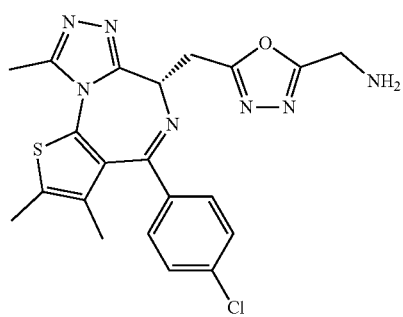

9
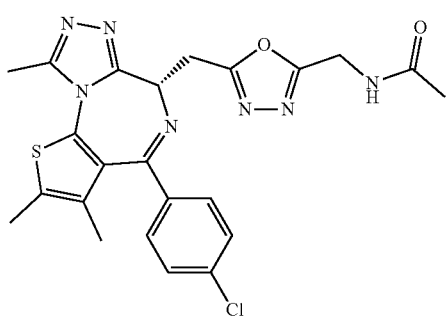
10
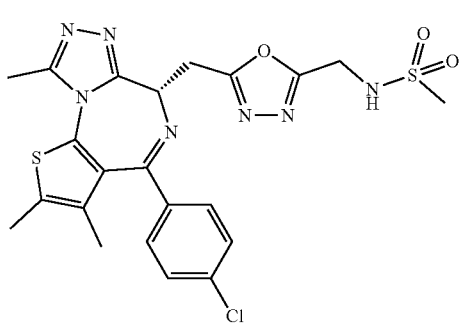
11
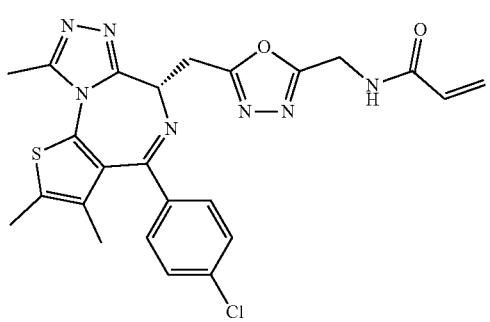
12
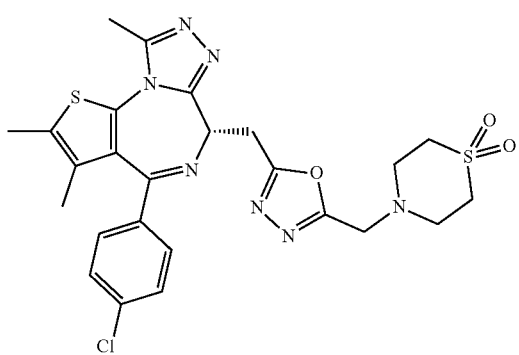
13
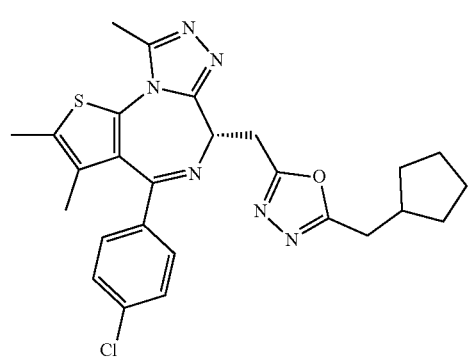
14
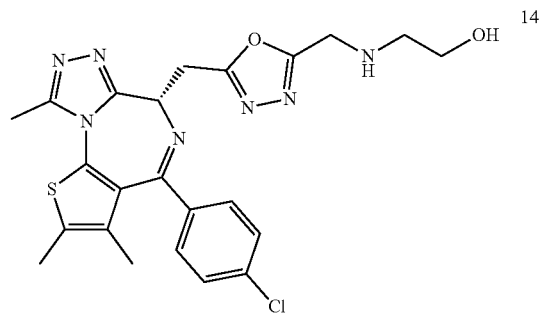
15
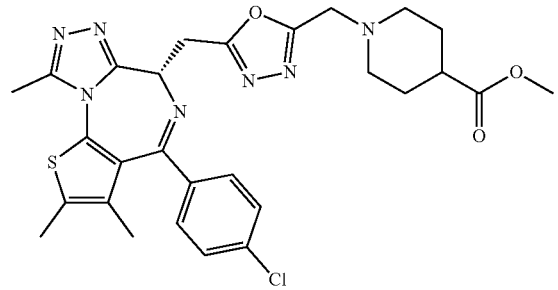
16
17
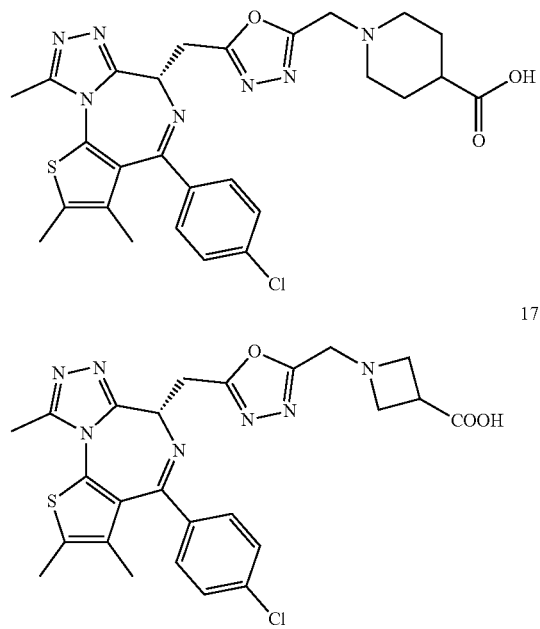

7
-continued
18
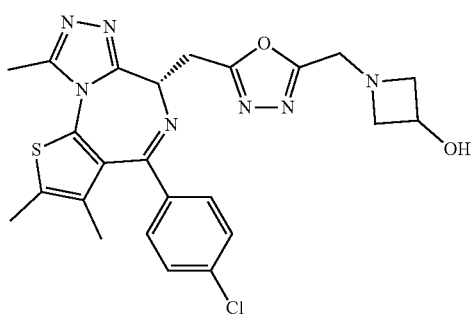
19
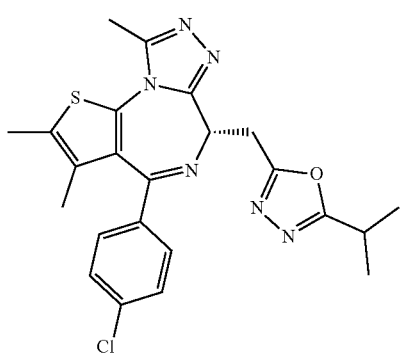
20
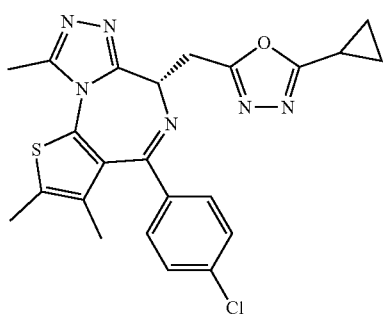
21
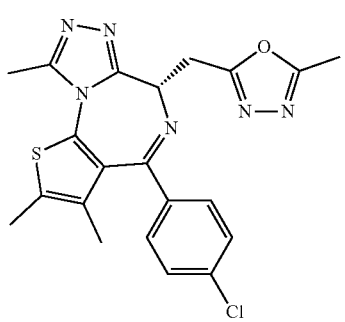
22
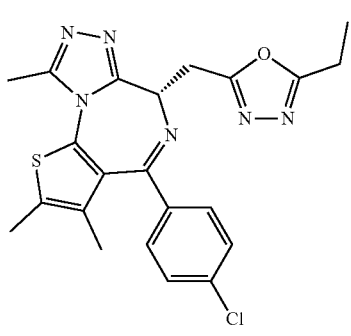
8
-continued
23
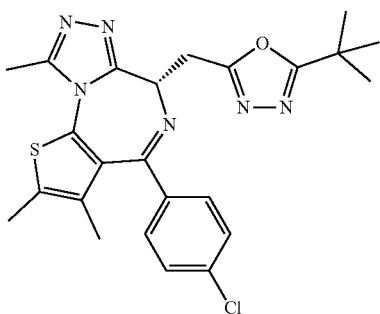
25
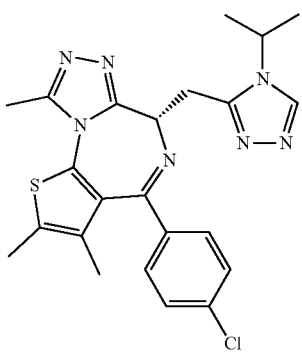
26
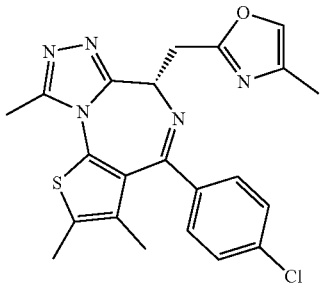
27
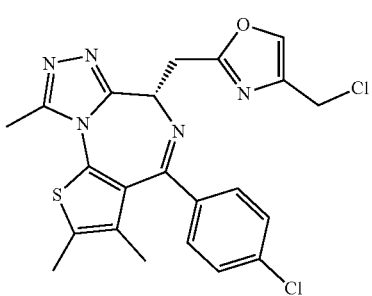
30
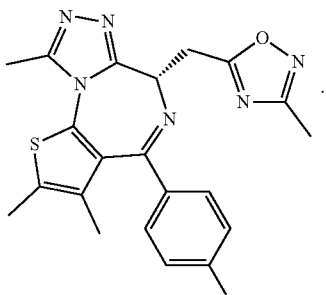
The method for preparation of above compounds include one of the following routes:

Scheme 1
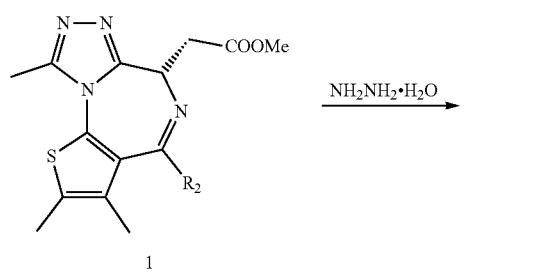 
1
NH₂NH₂•H₂O
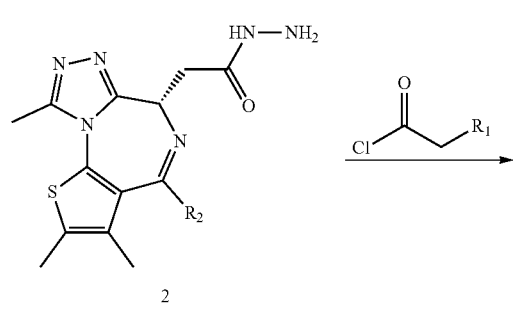
2
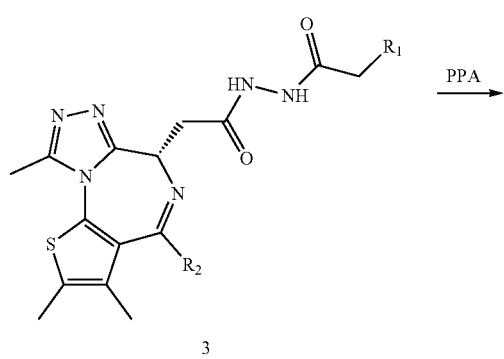
3
PPA
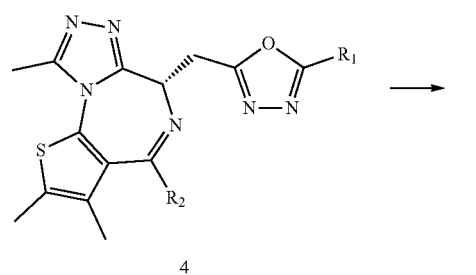
4
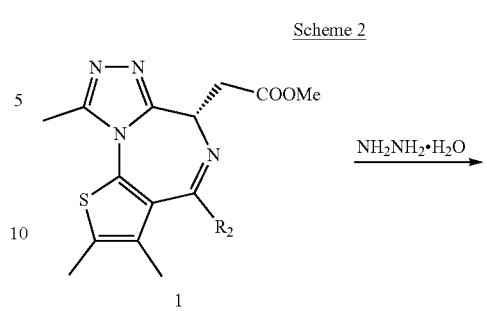
Scheme 2
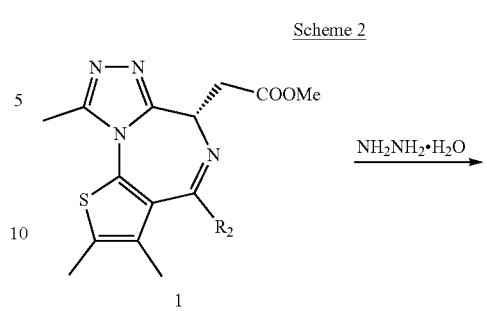
1
NH₂NH₂•H₂O
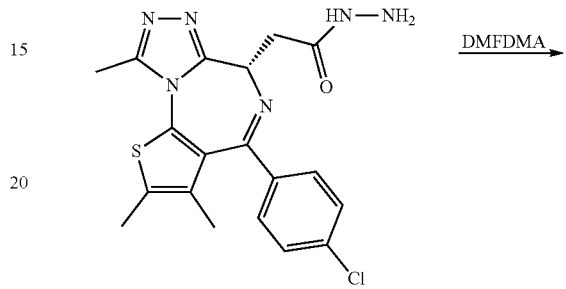
DMFDMA
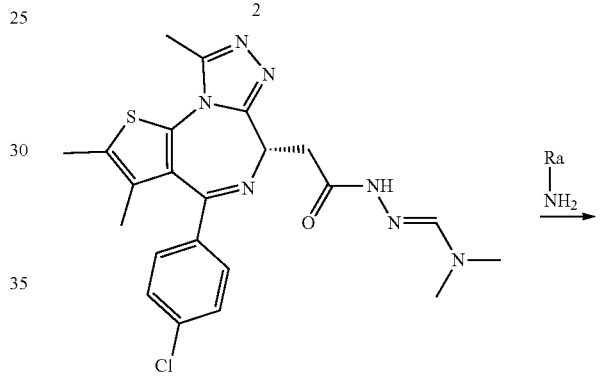
2
Ra—NH₂
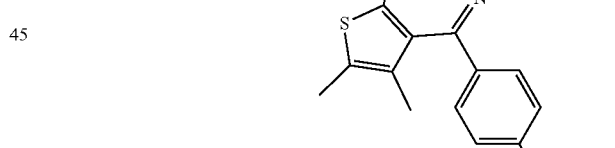
Scheme 3
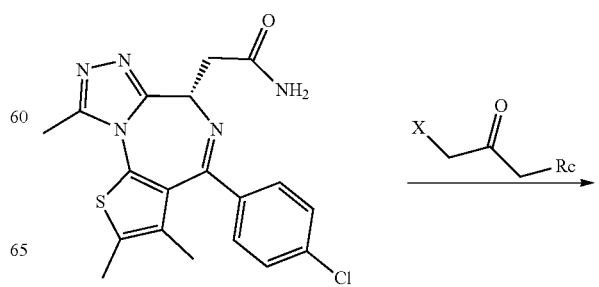

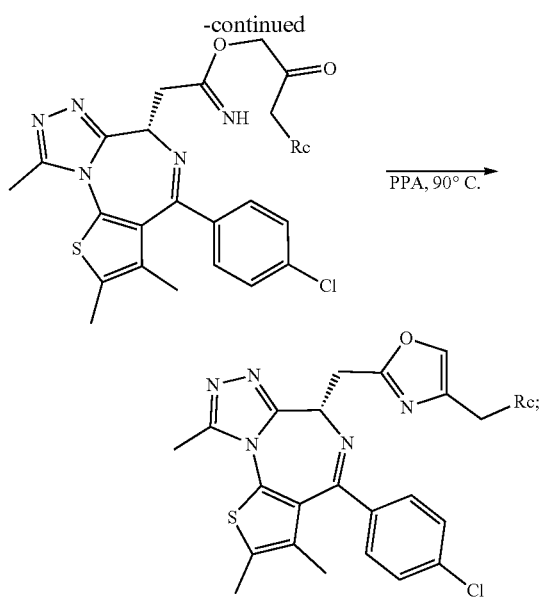

Wherein, X is halogen; Rc is H or C1-C5 alkyl;

Scheme 4

The use of above compounds, or a solvate thereof, or a pharmaceutically acceptable salt thereof in the preparation of a medicament for treatment of a disease or symptom associated with BET protein. Further, said BET protein-related diseases or symptoms are tumors, autoimmune or inflammatory, and viral infections.

Further, said tumors are breast cancer, brain cancer, cervical cancer, colorectal cancer, gastrointestinal cancer, esophageal cancer, liver cancer, lung cancer, pancreatic cancer, breast cancer, endometrial cancer, nasopharyngeal cancer, ovarian cancer, and prostate cancer.

Further, said autoimmune or inflammatory diseases are allergy, allergic rhinitis, arthritis, asthma, chronic obstructive pulmonary disease, degenerative arthritis, skin disease, organ rejection, eczema, hepatitis, inflammatory bowel disease, multiple sclerosis, myasthenia weakness, psoriasis, sepsis, systemic lupus erythematosus, tissue transplant rejection, and type I diabetes.

Further, said virus infection means being infected with the following viruses: adenovirus, hepatitis B virus, hepatitis C virus, herpes virus, human immunodeficiency virus, and human papilloma virus. Further, said tumor is prostate cancer.

A drug combination, that is a pharmaceutically common-used preparation prepared by using said compounds, or a solvate thereof, or a pharmaceutically acceptable salt thereof as active ingredients, together with addition of pharmaceutically acceptable adjuvants or auxiliary components.

The BRD4 inhibitor provided by the present invention has a good inhibitory effect on the proliferation of human prostate cancer cell line CWR22Rv1, indicating that the compound of the present invention can be used in the preparation of anti-tumor medicaments, especially those for treatment of prostate cancer.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

General procedure 1:

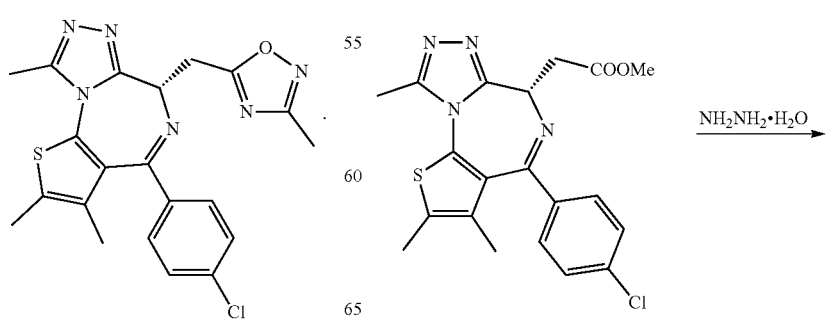

14

Example 1 Synthesis of Compound 4

1. Synthesis of (S)-2-(4-(4-chlorophenyl)-2,3,9-trimethyl-6H-thieno[3,2-f][1,2,4]triazolo[4,3-a][1,4]diaza-6-yl)acetylhydrazine (2)

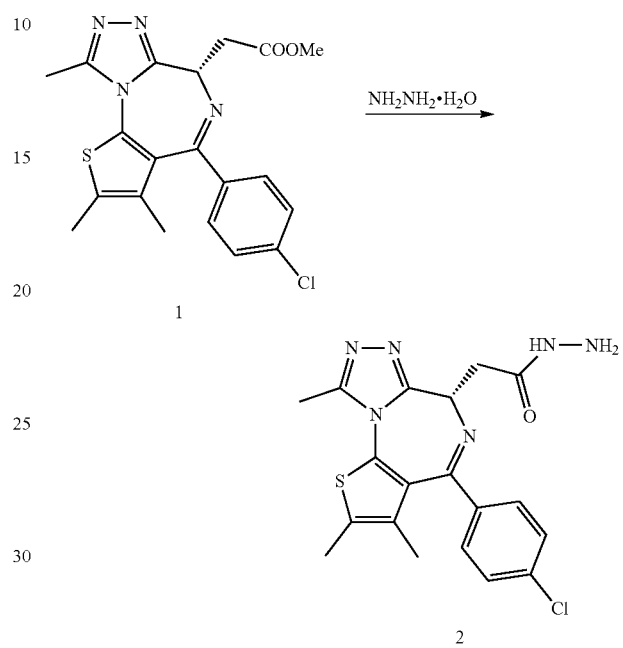

To a 50 mL reaction bottle, were added compound 1 (830 mg, 2 mmol) and MeOH (10 mL). After 5 minutes, hydrazine hydrate (1.5 mL) was added, and the mixture was allowed to react at 50° C. for 5 hours. After completion of the reaction, the reaction solution was poured into 50 mL water, and extracted with 30 mL (15 mL×3) dichloromethane. The organic phases were combined, dried with anhydrous sodium sulfate, and evaporated. The residue was purified by column chromatography to obtain compound 2 (750 mg, yield 90%). MS: m/z 415.9 [M+H]+.

2. Synthesis of (S)-2-chloro-N'-(2-(4-(4-chlorophenyl)-2,3,9-trimethyl-6H-thieno[3,2-f][1,2,4]triazolo[4,3-a][1,4]diaza-6-yl)acetyl)acetylhydrazine (3)

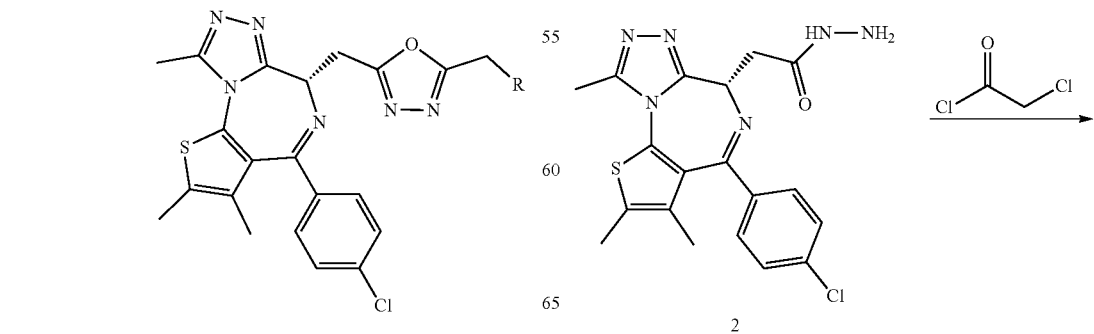

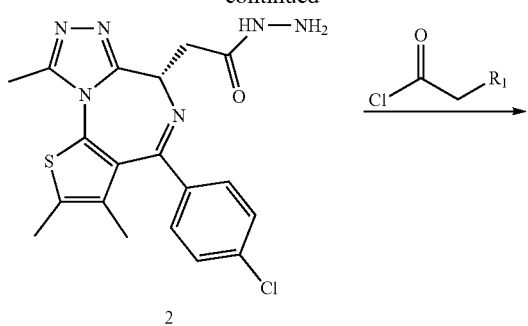

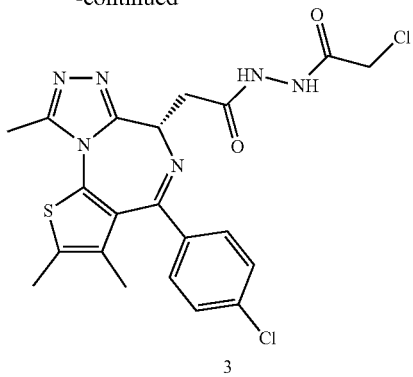

3

To a 50 mL reaction bottle, were added compound 2 (830 mg, 2 mmol), dichloromethane (10 mL), DIPEA (516 mg, 4 mmol), and chloroacetyl chloride (226 mg, 2 mmol) at 0° C. The mixture was allowed to react at 20° C. for 3 hours. After completion of the reaction, the reaction solution was poured into 50 mL water and extracted with 30 mL (15 mL×3) dichloromethane. The organic phases were combined, dried with anhydrous sodium sulfate, and evaporated. The residue was purified by column chromatography to obtain compound 3 (677 mg), with a yield of 69%. MS: m/z 491.2 [M+H]$^+$.

3. Synthesis of (S)-2-chloromethyl-5-((4-(4-chlorophenyl)-2,3,9-trimethyl-6H-thieno[3,2-f][1,2,4]triazolo[4,3-a][1,4]diaza-6-yl)methyl)-1,3,4-oxodiazole (4)

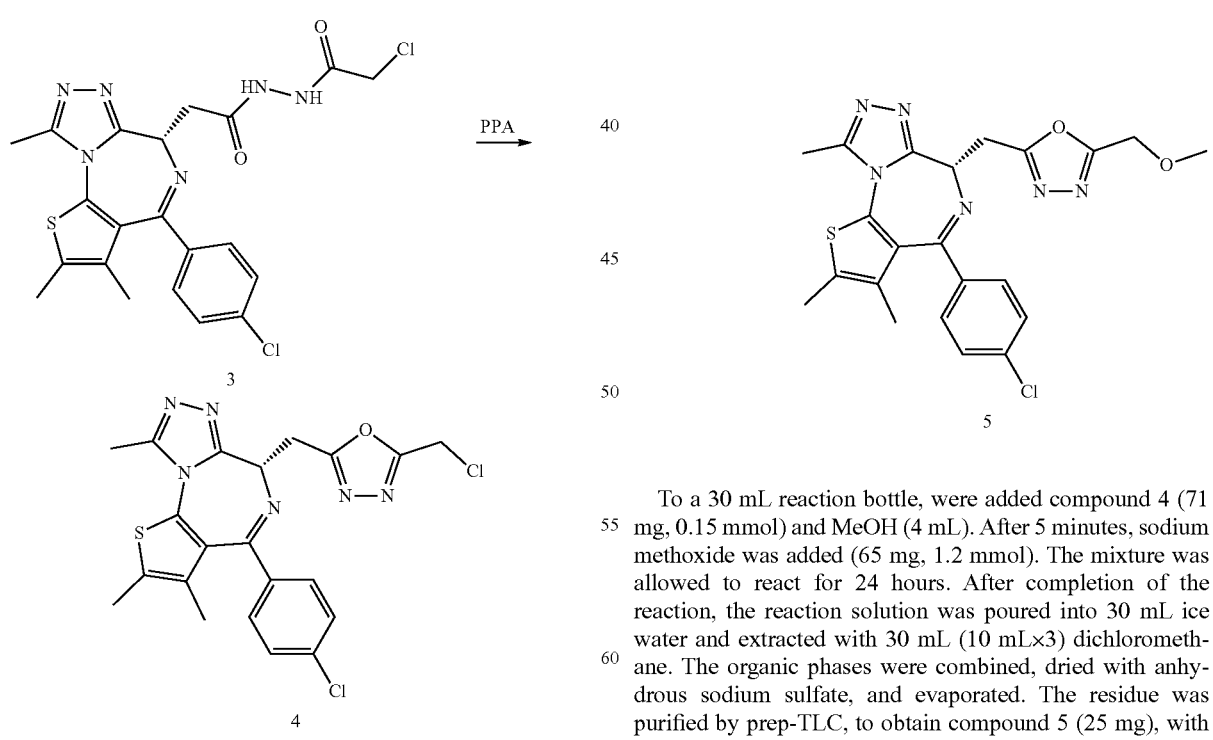

To a 30 mL reaction bottle, were added compound 3 (492 mg, 1 mmol) and PPA (4 mL). The mixture was allowed to react at 120° C. for 3 hours. After completion of the reaction, the reaction solution was poured into 50 mL ice water and extracted with 30 mL (10 mL×3) dichloromethane. The organic phase was combined, dried with anhydrous sodium sulfate, and evaporated. The residue was purified by column chromatography to obtain compound 4 (219 mg), with a yield of 46%. MS: m/z 473.2 [M+H]$^+$.

$^1$H NMR (400 MHz, CDCl$_3$) δ7.35 (q, J=8.7 Hz, 4H), 4.78 (dd, J=8.2, 6.2 Hz, 1H), 4.74 (s, 2H), 4.16 (t, J=6.9 Hz, 2H), 2.72(s, 3H), 2.42 (s, 3H), 1.68 (s, 3H).

Example 2 Synthesis of (S)-2-((4-(4-chlorophenyl)-2,3,9-trimethyl-6H-thieno[3,2-f][1,2,4]triazolo[4,3-a][1,4]diaza-6-yl)methyl)-5-(methoxylmethyl)-1,3,4-oxodiazole (5)

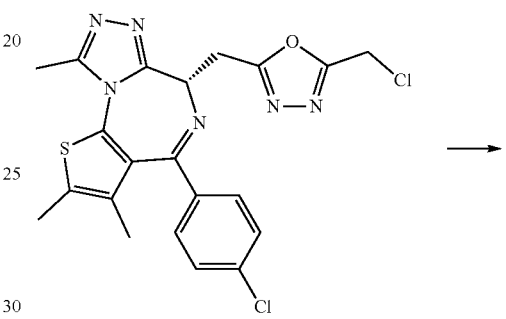

To a 30 mL reaction bottle, were added compound 4 (71 mg, 0.15 mmol) and MeOH (4 mL). After 5 minutes, sodium methoxide was added (65 mg, 1.2 mmol). The mixture was allowed to react for 24 hours. After completion of the reaction, the reaction solution was poured into 30 mL ice water and extracted with 30 mL (10 mL×3) dichloromethane. The organic phases were combined, dried with anhydrous sodium sulfate, and evaporated. The residue was purified by prep-TLC, to obtain compound 5 (25 mg), with a yield of 36%. MS: m/z 469.1 [M+H]$^+$.

$^1$H NMR (400 MHz, CDCl$_3$) δ7.35 (m, 4H), 4.81 (t, J=6.9 Hz, 1H), 4.67 (s, 2H), 4.15 (d, J=6.7 Hz, 2H), 3.48 (d, J=2.7 Hz, 3H), 2.72 (s, 3H), 2.42 (s, 3H), 1.69 (s, 3H).

Example 3 Synthesis of (S)-2-((4-(4-chlorophenyl)-2,3,9-trimethyl-6H-thieno[3,2-f][1,2,4]triazolo[4,3-a][1,4]diaza-6-yl)methyl)-5-(ethoxylmethyl)-1,3,4-oxodiazole (6)

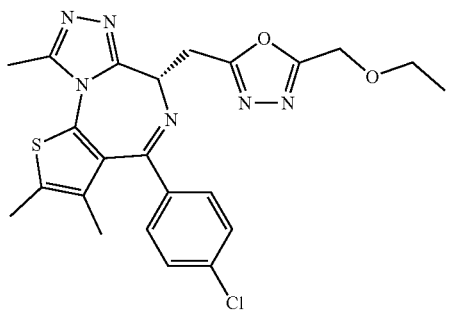

6

The synthetic method of compound 6 is same to that of compound 5, using the corresponding reagents. MS: m/z 469.1 [M+H]⁺.

¹H NMR (400 MHz, CDCl₃) δ7.35 (m, 4H), 4.82 (s, 1H), 4.71 (s, 2H), 4.15 (d, J=6.5 Hz, 2H), 3.66 (q, J=7.0 Hz, 2H), 2.74 (s, 3H), 2.43 (s, 3H), 1.69 (s, 3H), 1.26 (t, J=7.0 Hz, 3H).

Example 4 Synthesis of (S)-(5-((4-(4-chlorophenyl)-2,3,9-trimethyl-6H-thieno[3,2-f][1,2,4]triazolo[4,3-a][1,4]diaza-6-yl)methyl)-1,3,4-oxodiazole-2-yl)methanol (7)

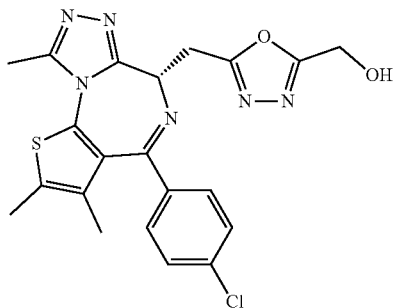

7

The synthetic method of compound 7 is same to that of compound 5, using the corresponding reagents. MS: m/z 455.1 [M+H]⁺.

¹H NMR (CDCl₃, 400 MHz): δ7.390-7.308 (m, 4H), 4.880 (s,2H), 4.781 (t, 1H, J=7.2 Hz), 4.202-4.073 (m, 2H), 2.695 (s, 3H), 2.619 (s, 3H), 2.420 (s, 3H).

Example 5 Synthesis of (S)-(5-((4-(4-chlorophenyl)-2,3,9-trimethyl-6H-thieno[3,2-f][1,2,4]triazolo[4,3-a][1,4]diaza-6-yl)methyl)-1,3,4-oxodiazole-2-yl)methylamine (8)

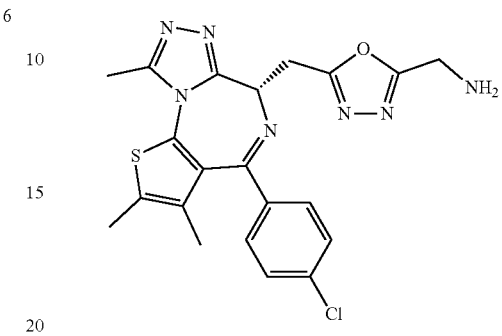

8

The synthetic method of compound 8 is same to that of compound 5, using the corresponding reagents. MS: m/z 454.1 [M+H]⁺.

¹H NMR (CDCl₃, 400MHz): δ7.410-7.307 (m, 4H), 4.890 (s, 2H), 4.791 (t, 1H, J=7.1 Hz), 4.012-3.718 (m, 2H), 2.698 (s, 3H), 2.629 (s, 3H), 2.410 (s, 3H).

Example 6 Synthesis of (S)-N-((5-((4-(4-chlorophenyl)-2,3,9-trimethyl-6H-thieno[3,2-f][1,2,4]triazolo[4,3-a][1,4]diaza-6-yl)methyl)-1,3,4-oxodiazole-2-yl) methyl)acetylamine (9)

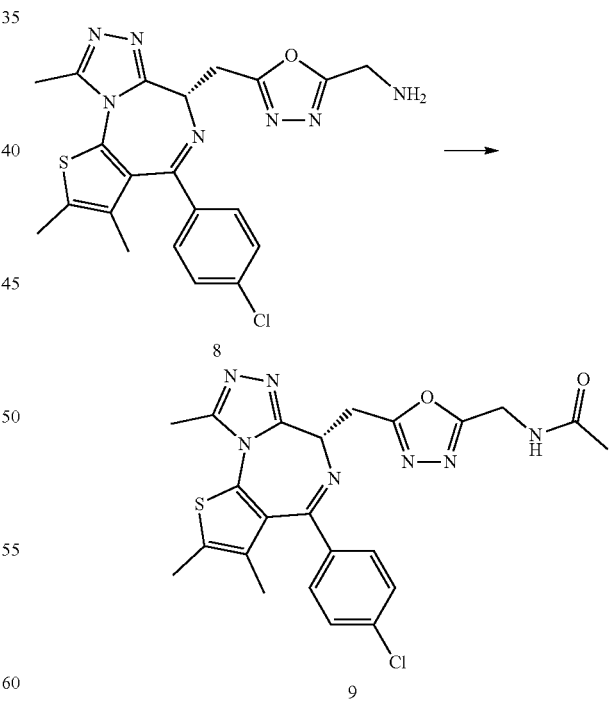

To a 30 mL reaction bottle, were added compound 8 (45 mg, 0.1 mmol), dichloromethane (5 mL), DIPEA (387 mg, 0.3 mmol), and acetyl chloride (16 mg, 0.2 mmol) at 0° C. The mixture was allowed to react at 20° C. for 3 hours. After completion of the reaction, the reaction solution was poured into 20 mL water and extracted with 30 mL (10 mL×3) dichloromethane. The organic phases were combined, dried with anhydrous sodium sulfate, and evaporated. The residue was purified by prep-TLC to obtain compound 9 (27 mg), with a yield of 55%. MS: m/z 496.2 [M+H]⁺.

¹HNMR (CDCl₃, 400 MHz): δ7.394-7.320 (m, 4H), 6.738 (s, 1H), 4.756 (t, 1H, J=6.8 Hz), 4.698 (d, 2H, J=6.4 Hz), 4.181-4.032 (m, 2H), 2.681 (s, 3H), 2.420 (s, 3H), 2.077 (s, 3H), 1.914 (s, 3H).

Example 7 Synthesis of (S)-N-((5-((4-(4-chlorophenyl)-2,3,9-trimethyl-6H-thieno[3,2-f][1,2,4]triazolo[4,3-a][1,4]diaza-6-yl)methyl) -1,3,4-oxodiazole-2-yl) methyl) methanesulfonamide (10)

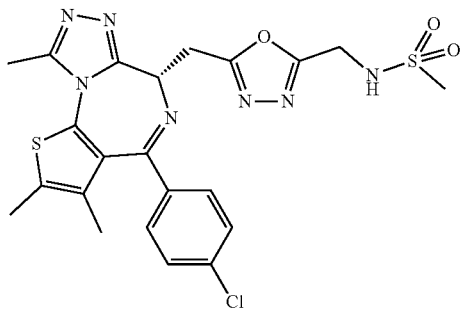

10

The synthetic method of compound 10 is same to that of compound 9, using the corresponding reagents. MS: m/z 532.1 [M+H]⁺.

¹H NMR (CDCl₃, 400 MHz): δ7.394-7.322 (m, 4H), 6.047 (s, 1H), 4.765 (t, 1H, J=6.8 Hz), 4.620 (d, 2H, J=5.2 Hz), 4.222-4.032 (m, 2H), 3.052 (s, 3H), 2.683 (s, 3H), 2.420 (s, 3H), 1.801 (s, 3H).

Example 8 Synthesis of (S)-N-((5-((4-(4-chlorophenyl)-2,3,9-trimethyl-6H-thieno[3,2-f][1,2,4]triazolo[4,3-a][1,4]diaza-6-yl)methyl)-1,3,4-oxodiazole-2-yl)methyl)acrylamide

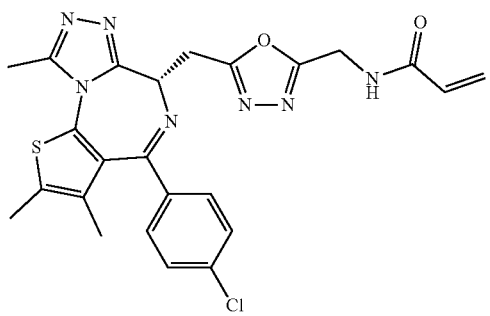

11

The synthetic method of compound 11 is same to that of compound 9, using the corresponding reagents. MS: m/z 508.2 [M+H]⁺.

¹HNMR (CDCl₃, 400 MHz): 7.390-7.319 (m, 4H), 6.735 (s, 1H), 6.389 (d, 1H, J=17.2 Hz), 6.240-6.171 (m, 1H), 5.741 (d, 1H, J=10 Hz), 4.782-4.745 (m, 3H), 4.185-4.043 (m, 2H), 2.685 (s, 3H), 2.420 (s, 3H), 1.76 (s, 3H).

Example 9 Synthesis of (S)-4-((5-((4-(4-chlorophenyl)-2,3,9-trimethyl-6H-thieno[3,2-f] [1,2,4]triazolo[4,3-a][1,4]diaza-6-yl)methyl)-1,3,4-oxodiazole-2-yl)methyl)thiomorpholine 1,1-dioxide (12)

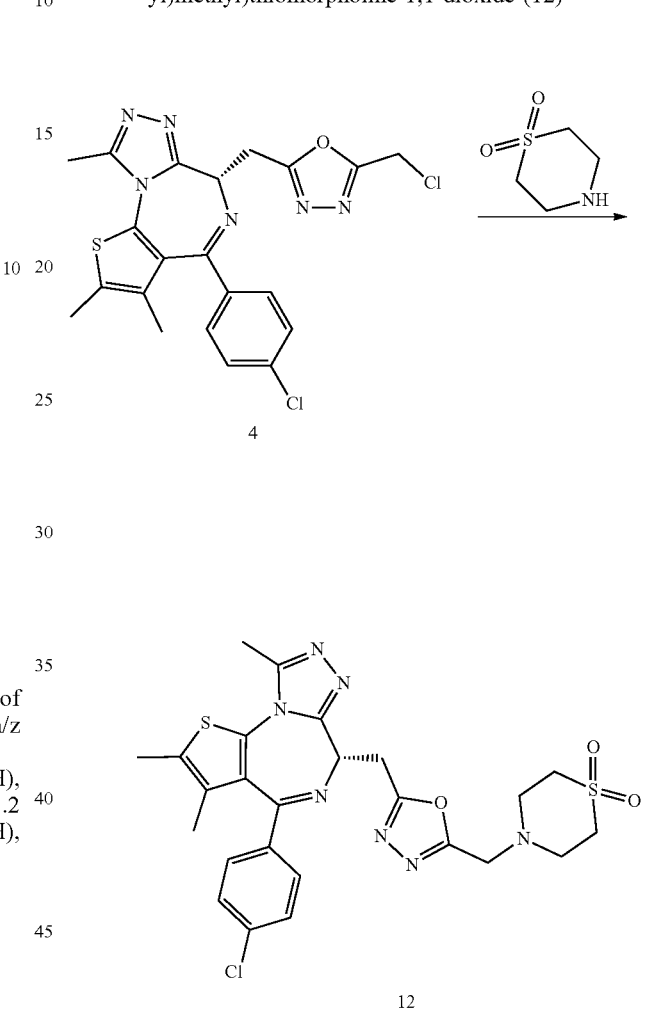

To a 30 mL reaction bottle, were added compound 4 (71 mg, 0.15 mmol), dichloromethane (5 mL), DIPEA (77 mg, 0.6 mmol), KI (30 mg, 0.18 mmol), thiomorpholine 1,1-dioxide, and KI (40 mg, 0.3 mmol). The mixture was allowed to react at room temperature for 24 hours. After completion of the reaction, the reaction solution was poured into 50 mL water and extracted with 30 mL (10 mL×3) dichloromethane. The organic phases were combined, dried with anhydrous sodium sulfate, and evaporated. The residue was purified by prep-TLC to obtain compound 12 (36 mg), with a yield of 43%.

MS: m/z 472.2 [M+H]⁺.

¹H NMR (400 MHz, CDCl₃): δ7.39 (d, J=8.0 Hz, 2H), 7.33 (d, J=8.0 Hz, 2H), 4.79 (s, 1H), 4.14 (m, 2H), 4.00 (s, 2H), 3.09 (s, 4H), 3.05 (s, 4H), 2.70 (s, 3H), 2.42 (s, 3H), 1.70 (s, 3H).

Example 10 Synthesis of 5-((5-(((S)-4-(4-chlorophenyl)-2,3,9-trimethyl-6H-thieno[3,2-f][1,2,4]triazolo[4,3-a][1,4]diaza-6-yl)methyl)-1,3,4-oxodiazole-2-yl)methyl)-2-oxo-5-azabicyclo[2.2.1]heptane (13)

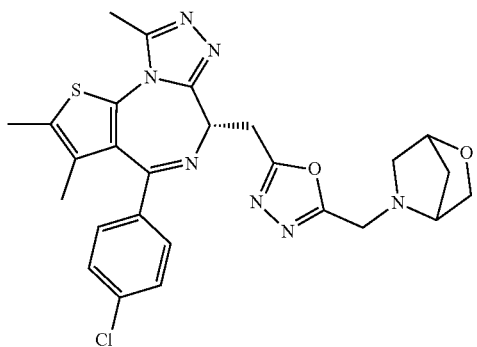

The synthetic method of compound 13 is same to that of compound 7, using the corresponding reagents.
MS: m/z 536.2 [M+H]$^+$.
$^1$H NMR (400 MHz, CDCl$_3$):δ7.35 (dd, J=21.6, 8.5 Hz, 4H), 4.79 (t, J=7.1 Hz, 1H), 4.45 (s, 1H), 4.22-3.93 (m, 5H), 3.68 (d, J=7.9 Hz, 1H), 3.63 (s, 1H), 3.05 (d, J=10.0 Hz, 1H), 2.79-2.72 (m, 1H), 2.68 (s, 3H), 2.42 (s, 3H), 1.91 (d, J=9.9 Hz, 1H), 1.80 (d, J=9.7 Hz, 1H), 1.68 (s, 3H).

Example 11 Synthesis of (S)-2-(((5-((4-(4-chlorophenyl)-2,3,9-trimethyl-6H-thieno[3,2-f][1,2,4]triazolo[4,3-a][1,4]diaza-6-yl)methyl)-1,3,4-oxodiazole-2-yl)methyl)amino)ethanol (14)

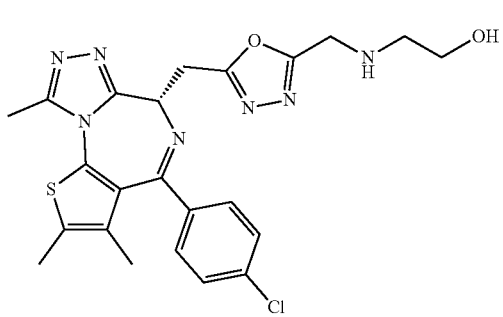

The synthetic method of compound 14 is same to that of compound 7, using the corresponding reagents. MS: m/z 498.0 [M+H]$^+$.
$^1$H NMR (400 MHz, CDCl$_3$) δ7.40 (d, J=8.8, 2H), 7.34 (d, J=8.8, 2H), 4.78 (t, J=7.2,1H), 4.21 (dd, J=7.6, 16.0, 1H), 4.15 (s, 2H), 4.05 (dd, J=7.6, 16.0, 1H), 3.71 (t, J=5.0, 2H), 2.93-2.87(m, 2H), 2.67 (s, 3H), 2.41 (s, 3H), 1.69 (s, 3H).

Example 12 Synthesis of (S)-methyl-1-((5-((4-(4-chlorophenyl)-2,3,9-trimethyl-6H-thieno[3,2-f][1,2,4]triazolo[4,3-a][1,4]diaza-6-yl)methyl) -1,3,4-oxodiazole-2-yl)methyl)piperidin-4-carboxylic ester (15)

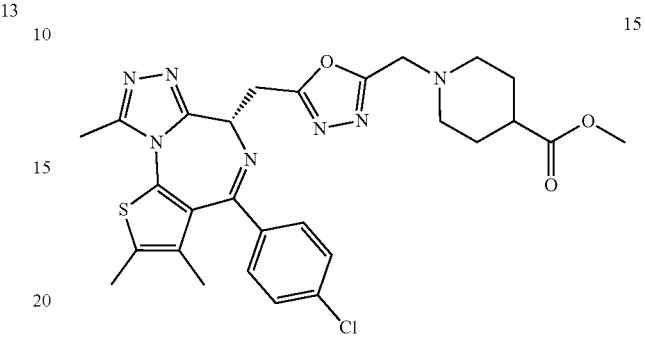

The synthetic method of compound 15 is same to that of compound 7, using the corresponding reagents. MS: m/z 580.2 [M+H]$^+$.
$^1$H NMR (400 MHz, CDCl$_3$) δ7.38 (d, J=8.8, 2H), 7.33 (d, J=8.8, 2H), 4.78 (t, J=7.2, 1H), 4.14 (dd, J=8.0, 2.8, 2H), 3.85 (s, 2H), 3.68 (s, 3H), 2.96 (m, 2H), 2.67 (s, 3H), 2.41 (s, 3H), 2.27 (br, 2H),1.95-1.83 (m, 4H), 1.69 (s, 3H).

Example 13 Synthesis of (5)-1-((5-((4-(4-chlorophenyl)-2,3,9-trimethyl-6H-thieno[3,2-f][1,2,4]triazolo[4,3-a][1,4]diaza-6-yl)methyl)-1,3,4-oxodiazole-2-yl)methyl)piperidin-4-carboxylic acid (16)

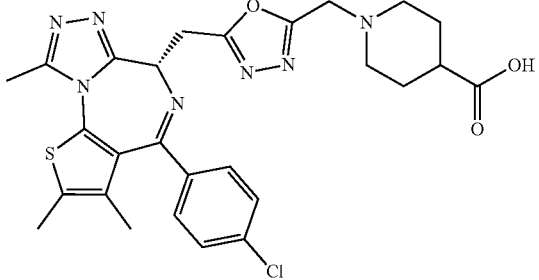

The synthetic method of compound 16 is same to that of compound 7, using the corresponding reagents. MS: m/z 566.2 [M+H]$^+$.
$^1$H NMR (400 MHz, CDCl$_3$) δ7.38 (d, J=8.8 Hz, 2H), 7.33 (d, J=8.8, 2H), 4.78 (t, J=7.2 Hz,1H), 4.14 (dd, J=8.0, 2.8 Hz, 2H), 3.85 (s, 2H), 2.96 (m, 2H), 2.67 (s, 3H), 2.41 (s, 3H), 2.30 (br, 2H), 1.99-1.87 (m, 4H), 1.69 (s, 3H).

Example 14 Synthesis of (5)-1-((5-((4-(4-chlorophenyl)-2,3,9-trimethyl-6H-thieno[3,2-f][1,2,4]triazolo[4,3-a][1,4]diaza-6-yl)methyl)-1,3,4-oxodiazole-2-yl)methyl)azacyclobutane-3-carboxylic acid (17)

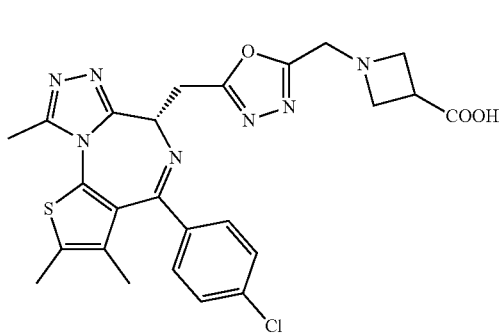

The synthetic method of compound 17 is same to that of compound 7, using the corresponding reagents. MS: m/z 566.2 [M+H]⁺.

Example 15 Synthesis of (5)-1-((5-((4-(4-chlorophenyl)-2,3,9-trimethyl-6H-thieno[3,2-f][1,2,4]triazolo[4,3-a][1,4]diaza-6-yl)methyl)-1,3,4-oxodiazole-2-yl)methyl)azacyclobutane-3-ol (18)

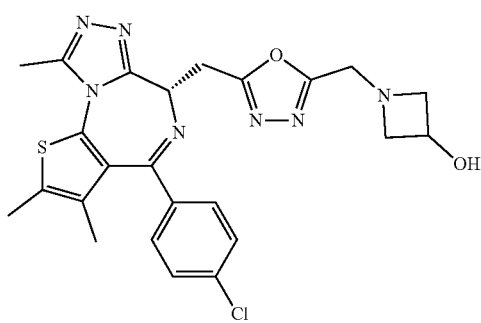

The synthetic method of compound 18 is same to that of compound 7, using the corresponding reagents. MS: m/z 510.2 [M+H]⁺.

¹H NMR (CDCl₃, 400MHz): δ7.413-7.322 (m, 4H), 4.804 (t, 1H, J=7.2 Hz), 4.480-4.419 (m, 1H), 4.215-4.156 (m, 1H), 4.067-4.008 (m, 1H), 3.948-3.852 (m, 2H), 3.785 (t, 1H, J=6.0 Hz), 3.708 (t, 1H, J=6.0 Hz), 3.345 (t, 1H, J=6.8 Hz), 3.049 (t, 1H, J=6.8 Hz), 2.660 (s, 3H), 2.617 (s, 3H), 2.418 (s, 3H).

Example 16 Synthesis of (S)-2-((4-(4-chlorophenyl)-2,3,9-trimethyl-6H-thieno[3,2-f][1,2,4]triazolo[4,3-a][1,4]diaza-6-yl)methyl)-5-isopropyl-1,3,4-oxodiazole (19)

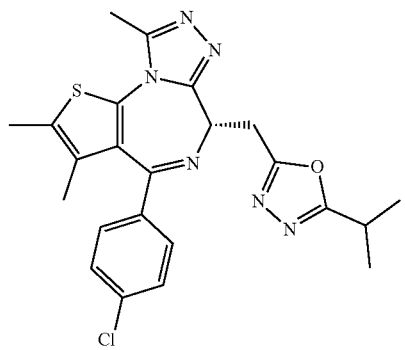

The synthetic method of compound 19 is same to that of compound 4, using the corresponding reagents. MS: m/z 467.2 [M+H]⁺.

¹H NMR (400 MHz, CDCl₃) δ7.34 (q, J=8.7 Hz, 4H), 4.79 (t, J=7.2 Hz, 1H), 4.10 (d, J=7.4 Hz, 2H), 3.30-3.14 (m, 1H), 2.72 (s, 3H), 2.42 (s, 3H), 1.68 (s, 3H), 1.43 (d, J=2.3 Hz, 3H), 1.41 (d, J=2.3 Hz, 3H). Example 17 Synthesis of (S)-2-((4-(4-chlorophenyl)-2,3,9-trimethyl-6H-thieno[3,2-f][1,2,4]triazolo[4,3-a][1,4]diaza-6-yl)methyl)-5-cyclopropyl-1,3,4-oxodiazole (20)

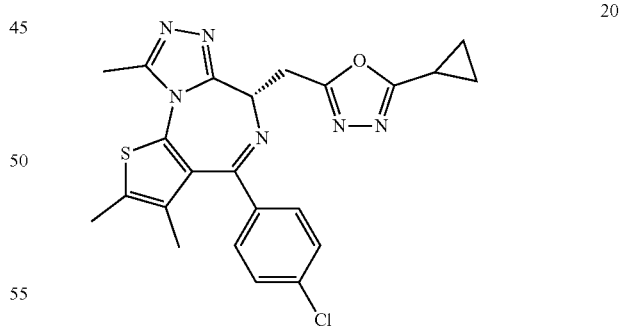

The synthetic method of compound 20 is same to that of compound 4, using the corresponding reagents.

MS: m/z 465.3 [M+H]⁺.

¹H NMR (400 MHz, CDCl₃) δ7.39 (m, 4H), 4.75 (dd, J=9.1, 5.1 Hz, 1H), 4.05 (m, 2H), 2.68 (s, 3H), 2.41 (s, 3H), 2.18 (m, 1H), 1.68 (s, 3H), 1.15 (m, 4H).

Example 18 Synthesis of (S)-2-((4-(4-chlorophenyl)-2,3,9-trimethyl-6H-thieno[3,2-f][1,2,4]triazolo[4,3-a][1,4]diaza-6-yl)methyl)-5-methyl-1,3,4-oxodiazole (21)

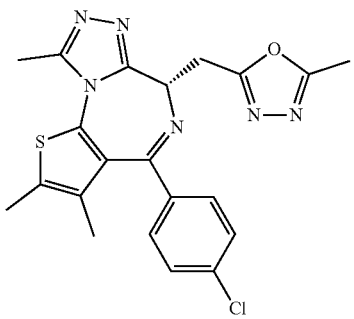

21

The synthetic method of compound 21 is same to that of compound 4, using the corresponding reagents. MS: m/z 439 [M+H]⁺.

¹H NMR (CDCl₃, 400 MHz): δ7.386-7.312 (m, 4H), 4.78 (t, 1H, J=7.2 Hz), 4.156-4.032 (m, 2H), 2.687 (s, 3H), 2.556 (s, 3H), 2.414 (s, 3H), 1.685 (s, 3H).

Example 19 Synthesis of (S)-2-((4-(4-chlorophenyl)-2,3,9-trimethyl-6H-thieno[3,2-f][1,2,4]triazolo[4,3-a][1,4]diaza-6-yl)methyl)-5-ethyl-1,3,4-oxodiazole (22)

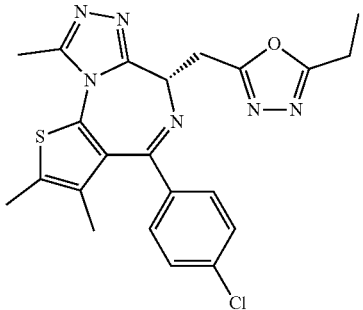

22

The synthetic method of compound 22 is same to that of compound 4, using the corresponding reagents. MS: m/z 453.2 [M+H]⁺.

¹H NMR (CDCl₃, 400 MHz): δ7.386-7.312 (m, 4H), 4.780 (t, 1H, J=7.2 Hz), 4.156-4.032 (m, 2H), 2.687 (s, 3H), 2.556 (s, 3H), 2.414 (s, 3H), 1.871 (q, 2H, J=6.4 Hz), 1.251 (t, 3H, J=6.4 Hz).

Example 20 Synthesis of (S)-2-(t-butyl)-5-((4-(4-chlorophenyl)-2,3,9-trimethyl-6H-thieno[3,2-f][1,2,4]triazolo[4,3-a][1,4]diaza-6-yl)methyl)-1,3,4-oxodiazole (22)

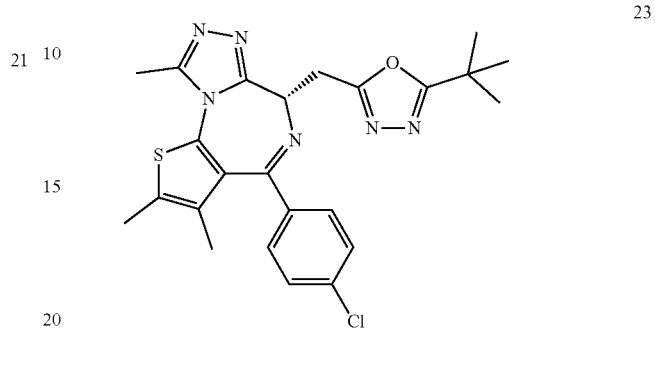

23

The synthetic method of compound 23 is same to that of compound 4, using the corresponding reagents. MS: m/z 481 [M+H]⁺.

¹H NMR (CDCl₃, 400 MHz): 7.386-7.312 (m, 4H), 4.780 (t, 1H, J=7.2 Hz), 4.156-4.032 (m, 2H), 2.687 (s, 3H), 2.556 (s, 3H), 2.414 (s, 3H), 1.255 (s, 9H).

Example 21 Synthesis of (S)-4-(4-chlorophenyl)-6-((4-isopropyl-4H-1,2,4-三唑-3-yl)methyl)-2,3,9-trimethyl-6H-thieno[3,2-f][1,2,4]triazolo[4,3-a][1,4]diazepine (25)

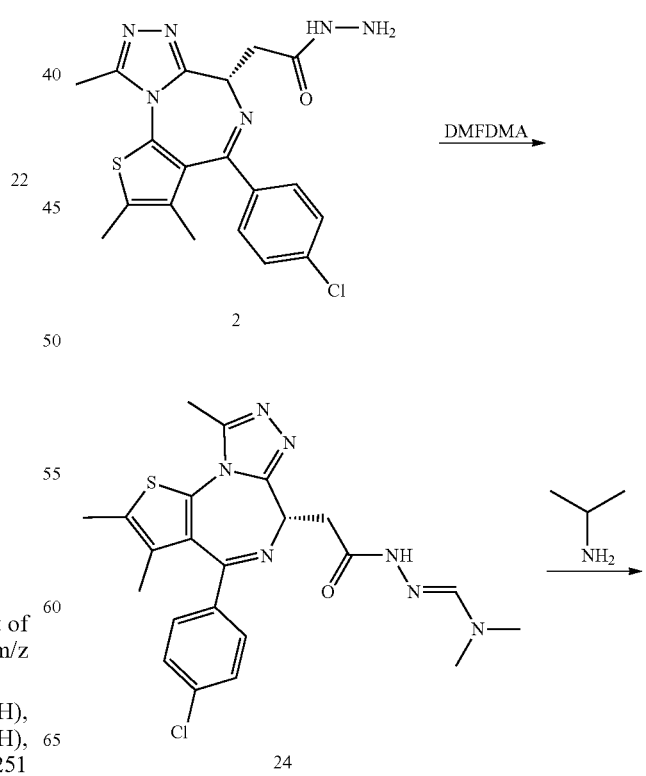

28

Example 22 Synthesis of (S)-2-(4-(4-chlorophenyl)-2,3,9-trimethyl-6H-thieno[3,2-f][1,2,4]triazolo[4,3-a][1,4]diaza-6-yl)-4-methyloxazole (26)

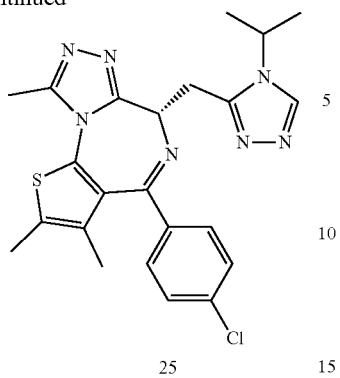

25

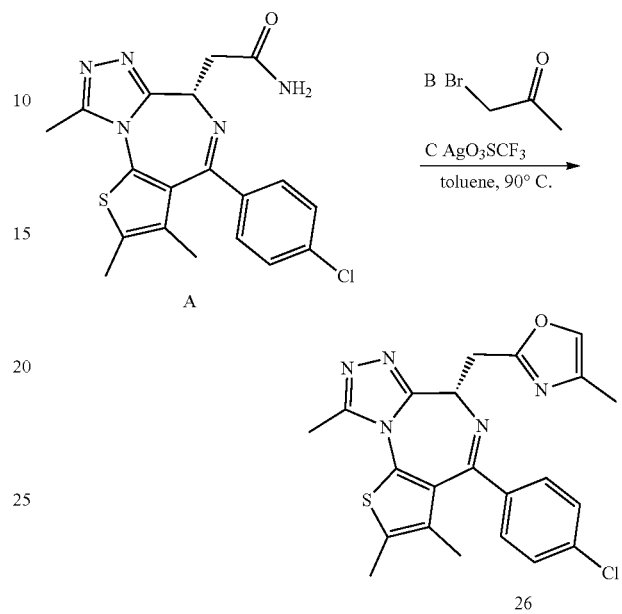

To a 30 mL reaction bottle, were added compound 2 (415 mg, 1 mmol), DMF (3 mL), and DMFDMA (595 mg, 5 mmol). The mixture was allowed to react at 110° C. for 6 hours. After completion of the reaction, the reaction solution was poured into 50 mL water and extracted with 30 mL (15 mL×3) dichloromethane. The organic phases were combined, dried with anhydrous sodium sulfate, and the solvent was rotary evaporated to obtain the intermediate 24.

To the intermediate 24, were added glacial acetic acid (5 mL) and isopropylamine (354 mg, 6 mmol). The mixture was allowed to react at 110° C. for 10 hours. After completion of the reaction, the reaction solution was poured into 30 mL water and extracted with 30 mL (15 mL×3) dichloromethane. The organic phases were combined, dried with anhydrous sodium sulfate, and evaporated. The residue was purified by column chromatography, to compound 25, with a total yield of 40% after two steps.

MS: m/z 466.2 [M+H]+.

General reaction procedure 2:

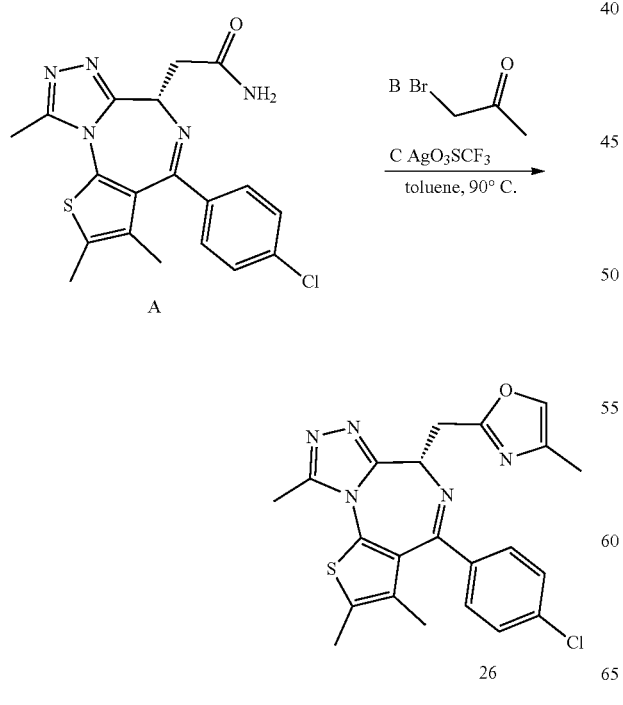

To a 10 mL sealed tube, were added compound A (100 mg, 0.25 mmol), toluene (3 mL), B (137 mg, 1 mmol), and C (128 mg, 0.5 mmol), and the mixture was allowed to react at 90° C. for 5 hours. The reaction solution was poured into 50 mL water, and extracted with 30 mL (15 mL×3) EA. The organic phases were combined, dried over anhydrous sodium sulfate, and evaporated. The residue was purified by column chromatography to obtain compound 26 (20 mg), with a yield of 18%. MS: m/z 438.1 [M+H]+.

General reaction procedure 3:

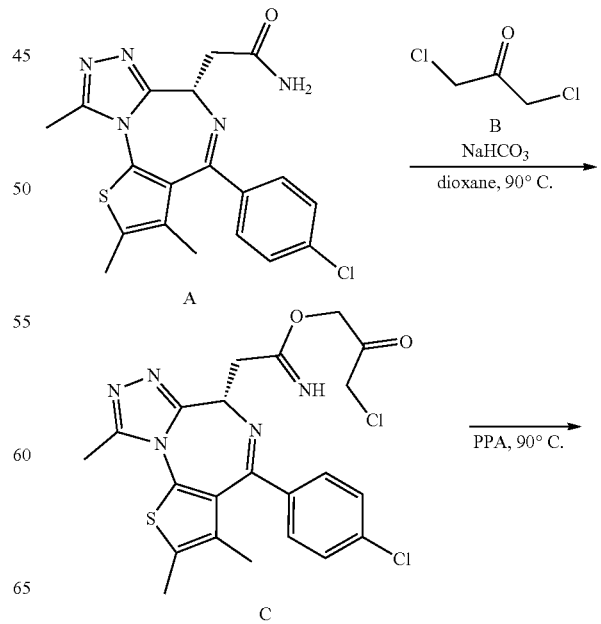

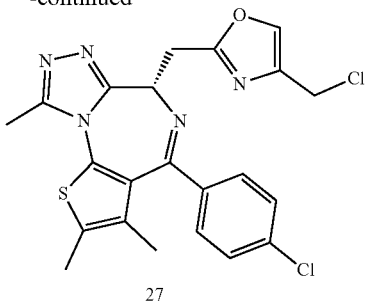

Example 23 (S) Synthesis of 2-(4-(4-chlorophenyl)-2,3,9-trimethyl-6H-thieno[3,2-f][1,2,4]triazolo[4,3-a][1,4]diaza-6-yl)-4-chloromethyloxazole (27)

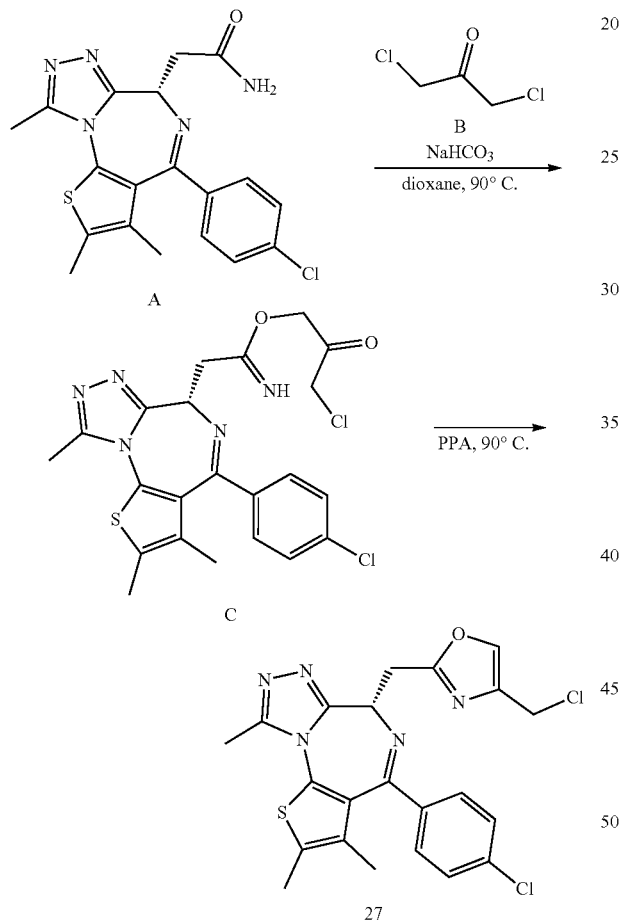

To a 10 mL sealed tube, were added compound A (200 mg, 0.5 mmol), dioxane (5 mL), B (127 mg, 1 mmol), and NaHCO₃ (168 mg, 2 mmol), and the mixture was allowed to react at 90° C. for 5 hours. The reaction solution was poured into 50 mL water, and extracted with 30 mL (15 mL×3) EA. The organic phases were combined, dried over anhydrous sodium sulfate, and evaporated. The residue was purified by column chromatography to obtain compound C (30 mg), with a yield of 12%. MS: m/z 490.1 [M+H]⁺.

The above intermediate C (30 mg, 0.07 mmol) and PPA (500 mg) were reacted at 90° C. for 1 hour. The reaction solution was poured into 50 mL water, and the pH was adjusted with NaOH to weak alkalinity, and extracted with 30 mL (15 mL×3) EA. The organic phases were combined, dried over anhydrous sodium sulfate, and purified by column chromatography to obtain compound 27 (18 mg), with a yield of 60%. MS: m/z 472.1 [M+H]⁺.

Example 24 Synthesis of (S)-5-((4-(4-chlorophenyl)-2,3,9-trimethyl-6H-thieno[3,2-f][1,2,4]triazolo[4,3-a][1,4]diaza-6-yl)methyl)-3-methyl-1,2,4-oxodiazole (29)

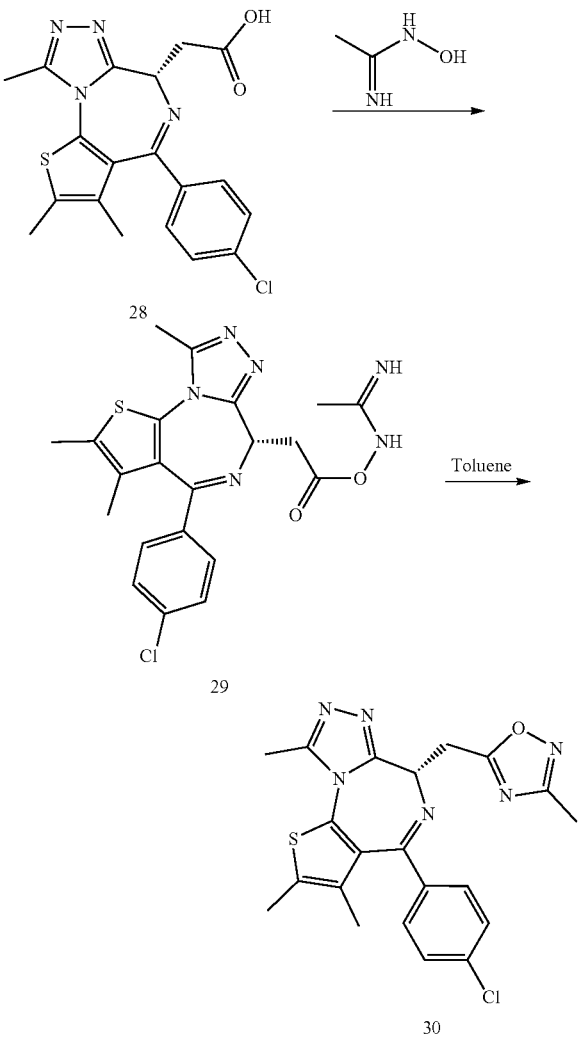

To a 10 mL eggplant-shaped flask, were add compound 28 (100 mg, 0.25 mmol), DCM (3 mL), N-hydroxyl cetamidine (37 mg, 0.5 mmol), HATU (190 mg, 0.5 mmol), and DIPEA (97 mg, 0.75 mmol). The mixture was allowed to react for 7 hours at room temperature. The reaction solution was poured into 10 mL water, and extracted with 15 mL (5 mL×3) DCM. The organic phases were combined, dried over anhydrous sodium sulfate, and evaporated. The residue was purified by column chromatography to obtain compound 29 (63 mg), with a yield of 55%. MS: m/z 457.1 [M+H]⁺. Above intermediate compound 29 was added to a 25 mL eggplant-shaped bottle, to which was then added 10 mL toluene. A water distributor was assembled on the eggplant-shaped bottle, and the bottle was heated to 120° C., to make the mixture react for about 5 hours. After completion of the reaction, compound 30 (26 mg) was obtained by purification via column chromatography, with a yield of 43%. MS: m/z 439.1 [M+H]$^+$.

$^1$H NMR (CDCl$_3$, 400 MHz): δ7.353-7.319 (m, 4H), 4.740 (s, 1H), 4.217-4.100 (m, 2H), 2.719 (s, 3H), 2.427 (s, 3H), 2.394 (s, 3H), 1.713 (s, 3H).

Hereinafter, the beneficial effects of the present invention are elucidated in the form of test examples.

Term Abbreviation and Definition mg milligram
mL milliliter
ug microgram
uL microliter
mM millimole
nM nanomole
DMSO dimethyl sulfoxide
Avg average value
SD standard deviation
DRC dose-effect curve Test Example 1 Inhibitory Effect of Compounds on BRD 1. Experimental Objective Homogeneous time-resolved fluorescence (HTRF) was used to detect the binding of the compound to BRD4 (D1 +D2) and BRDT (D1) proteins, and the AlphaScreen method was used to detect the binding of the compound to BRD2 (D1+D2) and BRD3 (D1+D2) proteins.

2. Experimental Background

Compounds were screened in vitro, and each concentration of the compound was diluted to 10 different concentrations. Four proteins, BRD4 (D1 +D2), BRDT (D1), BRD2 (D1+D2) and BRD3 (D1+D2), were selected to determine their IC$_{50}$ values (see Table 1).

3. Experimental Materials:
BRD2(1,2)(BPS, Cat.No.31024)
BRD3(1,2)(BPS, Cat.No.31035)
BRDT(D1)(Active Motif, Cat.No.31450)
BRD4(1,2)(BPS, Cat.No.31044)
(+)-JQ1(BPS, Cat.No.27402)

4. Compound Treatment:

The test compound was dissolved in dimethylsulfoxide (DMSO) and stored at a concentration of 10 mM.

5. Homogeneous Time-Resolved Fluorescence Detection Steps:

1) All compounds were gradiently diluted on Echo plate according to the arrangement of the test plate. The final concentration of DMSO was 0.1%.

2) Compounds or DMSO was transferred to a 384-well assay plate by using Echo autosampler.

3) 2× concentration of protein and peptide mixture was added to the assay plate.

4) 2× concentration of the mixed detection solution was added to the assay plate and shaken for 30 seconds.

5) The plate was incubated at room temperature for 2 hours.

6) The fluorescence signal was read on Envision microplate reader (with excitation light wavelength at 340 nm and emission light wavelength at 615 nm and 665 nm).

7) The curve was fitted.

The experimental data were entered into an Excel file, and the equation (1) was used to get the inhibitory rate.

$$\text{Inh \%} = (\text{Max} - \text{Signal}) / (\text{Max} - \text{Min}) \times 100 \quad \text{Equation (1)}$$

The resultant data were entered into GraphPad software, and the IC$_{50}$ value was obtained using equation (2).

$$Y = \text{Bottom} + (\text{Top} - \text{Bottom}) / (1 + 10^{((\text{LogIC50} - X) \times \text{Hill Slope})}) \quad \text{Equation (2)}$$

Wherein, Y-axis is the inhibition rate, while X-axis is the compound concentration.

6. AlphaScreen detection step:

1) Preparing 1-fold concentration of detection buffer 1-fold concentration of detection buffer was prepared (modified HEPES buffer).

2) Gradient dilution of compounds

The compound was transferred to the detection plate with an Echo autosampler for gradient dilution, so that the final concentration of dimethyl sulfoxide was 0.1%.

3) Preparation of protein solution

The protein was dissolved in a 1-fold concentration of detection buffer.

4) Preparation of substrate solution

The peptide was dissolved in 1-fold concentration of detection buffer to prepare a substrate solution.

5) 5 μL protein solution was transferred to the assay plate, and 5 μL 1-fold concentration of detection buffer was placed in the negative control well.

6) The plate was incubated at room temperature for 15 minutes.

7) 5 μL substrate solution was added to each well to start the reaction.

8) The plate was incubated at room temperature for 60 minutes.

9) Acceptor and donor solutions were prepared in 1-fold concentration of assay buffer.

15 μL acceptor and donor solution were added, respectively, and the plate was incubated at room temperature for 60 minutes without light.

10) The end point was read in EnSpire and Alpha mode.

11) The curve was fitted.

The experimental data were entered into an Excel file, and the equation (1) was used to get the inhibitory rate.

$$\text{Inh \%} = (\text{Max} - \text{Signal}) / (\text{Max} - \text{Min}) \times 100 \quad \text{Equation (1)}$$

The resultant data were entered into GraphPad software, and the IC$_{50}$ value was obtained using equation (2).

$$Y = \text{Bottom} + (\text{Top} - \text{Bottom}) / (1 + 10^{((\text{LogIC50} - X) \times \text{Hill Slope})}) \quad \text{Equation (2)}$$

Wherein, Y-axis is the inhibition rate, while X-axis is the compound concentration.

TABLE 1

| | IC$_{50}$ values of compounds against BRD | | | |
|---|---|---|---|---|
| | BRD2(1, 2) (uM) | BRD4(1, 2) (uM) | BRD3(1, 2) (uM) | BRDT(D1) (uM) |
| 20 | 0.0101 | 0.0254 | 0.020 | 0.049 |
| 6 | 0.015 | 0.027 | 0.020 | 0.046 |
| 19 | 0.0083 | 0.021 | 0.017 | 0.051 |
| 22 | 0.0108 | 0.025 | 0.021 | 0.046 |

Test Example 2 Biological Determination of the Inhibitory Effect of the Compound on CWR22RV1 Cell Proliferation Experimental Materials:
CWR22RV1 cell line (Cell bank of Chinese Academy of Sciences, TCHu100)
FBS (Gibco, Cat. No. 10099-141)
0.01M PBS (Biosharp, Cat. No. 162262)
RIPM1640 (Hyclone, Cat. No. 308090.01)
Penicillin-Streptomycin (Hyclone, Cat. No. SV30010)
Cell counting kit-8(Signalway Antibody, Cat. No. CP002)
DMSO (Sigma, Cat. No. D5879)
Centrifuge Tube, 15 ml (Excell Bio, Cat. No. CS015-0001)
Cell Culture Dish, (Excell Bio, Cat. No. CS016-0128)
96-well cell culture cluster (Corning, Cat. No. 3599)
Experimental Method:
1. Preparation of Buffer

| Cell culture medium | PBS buffer |
| --- | --- |
| RIPM1640 medium 10% FBS 1% Pen Strep | PBS powder was dissolved in 2 L ultrapure water and sterilized. |

2. Experimental Procedures:
(1) CWR22RV1 cells were subcultured with cell culture medium, and well-growth cells were inoculated in 96-well plates, with 80 μL per well. The number of cells in each well was 1500, and the plate was cultured overnight in a 37° C., 5% $CO_2$ cell incubator.
(2) The drug was prepared as a 30 mM stock solution using dimethyl sulfoxide (DMSO). before use, the stock solution was diluted 3 times with DMSO, and then diluted by a 3 times gradient to obtain 9 concentration gradients. The compound at each concentration was further diluted 200 times with the culture solution (to ensure that the DMSO concentration in the culture system was 0.1%), and each concentration was repeated 2 wells. 20 μL of the diluted compound was added to the cell culture wells (with final concentrations of 10 μM, 3.3 μM, 1.1 μM . . . ), and gently shaked to mix. In addition, three negative control wells containing only cells and three blank control wells containing only culture medium (6 wells each containing 20 μL DMSO 200-fold diluted with culture medium) were set.
3. Result Detection:
(1) After being cultured for 6 days, 10 μL CCK-8 was added to each well, and the cells were further cultured in a 5% $CO_2$ cell incubator at 37° C. for 2.5 hours.
(2) The absorbance (OD value) was measured at 450 nm with a multifunctional microplate reader.
(3) The data were analyzed with the Dose-response-inhibition equation in the software GraphPad Prism6, and $IC_{50}$ values were obtained. The $IC_{50}$ values (nM) of the compounds inhibiting the activity of CWR22RV1 is listed in Table 1.

TABLE 1

| $IC_{50}$ values (nM) of compounds on CWR22RV1 | |
| --- | --- |
| Compounds | $IC_{50}$ (nM) |
| Compound 4 | 28 |
| Compound 5 | 45 |
| Compound 6 | 61 |
| Compound 7 | 89 |
| Compound 9 | 110 |
| Compound 10 | 63 |
| Compound 11 | 54 |
| Compound 12 | 110 |
| Compound 14 | 163 |
| Compound 15 | 59 |
| Compound 16 | 2650 |
| Compound 17 | 2380 |
| Compound 18 | 89 |
| Compound 19 | 28 |
| Compound 20 | 37 |
| Compound 21 | 33 |
| Compound 22 | 47 |
| Compound 23 | 179 |
| Compound 25 | 1313 |
| Compound 26 | 264 |
| Compound 27 | 29 |
| Compound 30 | 47 |

The above results indicated that the compound provided in the present invention has a very good inhibitory effect on the proliferation of human prostate cancer cell CWR22RV1, suggesting that the compound of the present invention can be used in the preparation of antitumor drugs, especially drugs for treatment of prostate cancer.

The invention claimed is:
1. A compound of formula (I), or a pharmaceutically acceptable salt thereof:

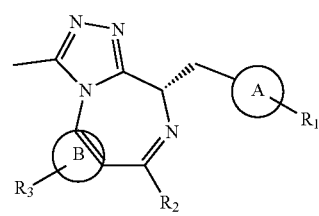

I wherein,
ring A represents a 5 membered aromatic ring or heteroaromatic ring;
$R_1$ represents 0-3 substituents in ring A and is selected from hydrogen, halogen, C1-C8 alkyl, C1-C8 haloalkyl, C1-C8 alkoxy, C3-C8 cycloalkyl, substituted aryl, substituted heteroaryl, C3-C8 heterocycloalkyl, —$(CH_2)_mO(CH_2)_nH$, —$(CH_2)_mCO(CH_2)_nH$, —$(CH_2)_mSO_2(CH_2)_nH$, —$(CH_2)_mCO_2(CH_2)_nH$, —$(CH_2)_mCONH(CH_2)_nH$, —$(CH_2)_mNH(CH_2)_nH$, —$(CH_2)_mSO_2NH(CH_2)_nH$,

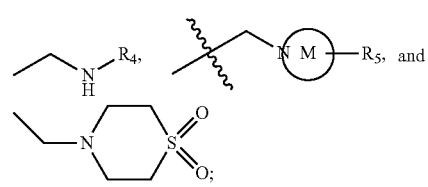

m and n are each independently selected from integers of 0-5;
R₄ is selected from H, —C(=O)Ra, —Ra—OH,

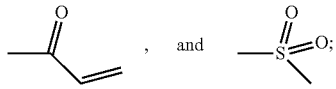, and 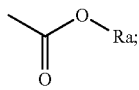;

M represents a 3-7 membered ring containing nitrogen atom;
R₅ represents 0-3 substituents in ring M and is selected from H, C1-C5 alkyl, hydroxyl, halogen, carboxyl, and

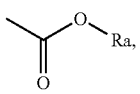

Ra represents C1-C5 alkyl or alkylenyl;
ring B is a 5-6 membered aromatic ring or heteroaromatic ring containing S atom;
ring B, together with the seven membered heterocycle linkage with it, shares two carbon atoms;
R₃ represents 0-3 substituents in ring B and is selected from H, halogen, C1-C8 alkyl, C1-C8 cycloalkyl, and C1-C8 alkoxyl; and
R₂ represents a benzene ring with 1-3 substituents, and the substituents are selected from halogen, hydroxyl, C1-C5 alkyl, and C1-C5 alkoxyl.

2. The compound or the pharmaceutically acceptable salt according to claim 1, wherein ring B is a five-membered heteroaromatic ring containing S atom.

3. The compound the pharmaceutically acceptable salt according to claim 1, wherein ring B has two substituents.

4. The compound or the pharmaceutically acceptable salt according to claim 3, wherein the substituent in ring B is methyl.

5. The compound or the pharmaceutically acceptable salt according to claim 1, wherein R₂ is a mono-substituted benzene ring.

6. The compound or the pharmaceutically acceptable salt according to claim 5, wherein R₂ is a halogenated benzene.

7. The compound or the pharmaceutically acceptable salt according to claim 1, wherein said compound has a structure of formula (II):

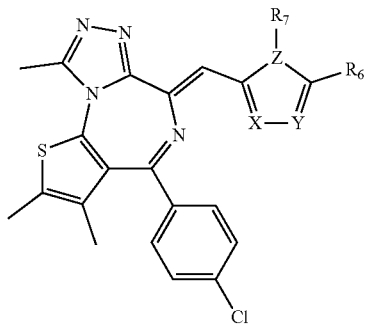

wherein,
X, Y, Z are each independent C or a heteroatom;
R₆ is independently selected from H, C1-C5 alkyl, C3-C5 cycloalkyl, C1-C5 haloalkyl, —(CH₂)ₘO(CH₂)ₙH,

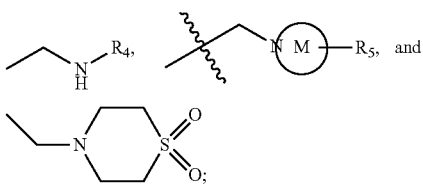

m and n are each independently selected from integers of 0-5 ;
R4 is selected from H, —C(=O)Ra, —Ra—OH,

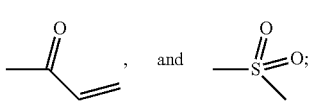;

M represents a 3-7 membered ring having nitrogen atom;
R₅ represents 0-3 substituents in ring M and is selected from H, hydroxyl, carboxyl, and wherein Ra represents C1-C5 alkyl or C1-C5 alkylenyl; and
R₇ is absent or C1-C5 alkyl, C1-C5 alkoxyl.

8. The compound or the pharmaceutically acceptable salt according to claim 7, wherein X, Y, and Z are each independently selected from C, N, and O.

9. The compound or the pharmaceutically acceptable salt according to claim 7, wherein m and n are independently selected from integers of 0-3.

10. The compound or the pharmaceutically acceptable salt according to claim 7, wherein R₇ is absent or isopropyl.

11. The compound or the pharmaceutically acceptable salt according to claim 7, wherein M is a 4-6 membered aliphatic ring.

12. The compound or the pharmaceutically acceptable salt according to claim 7, wherein ring M has one N atom.

13. The compound or the pharmaceutically acceptable salt according to claim 1, wherein said compound has structures as follow:

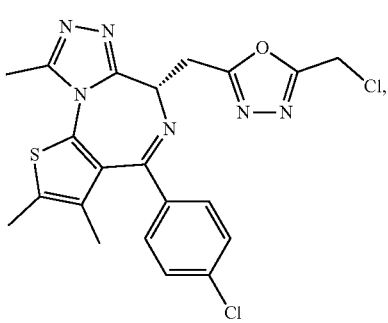

37
-continued
5
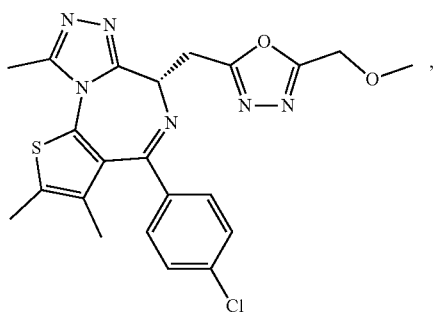
6
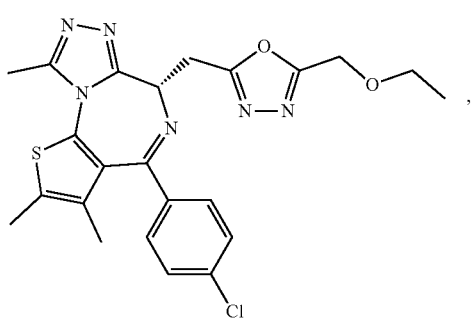
7
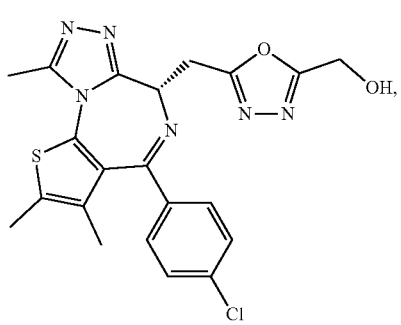
8
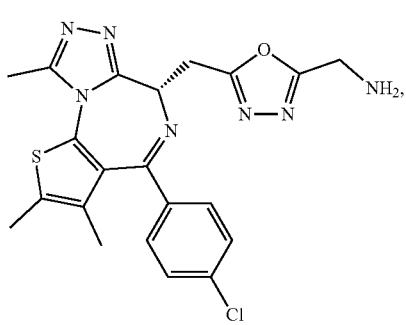
9
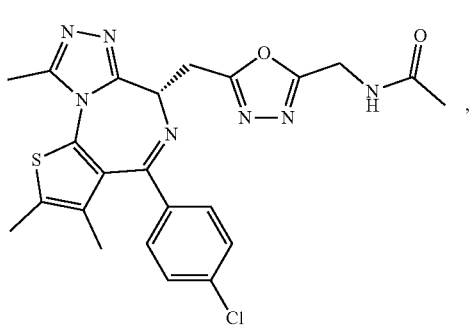
38
-continued
10
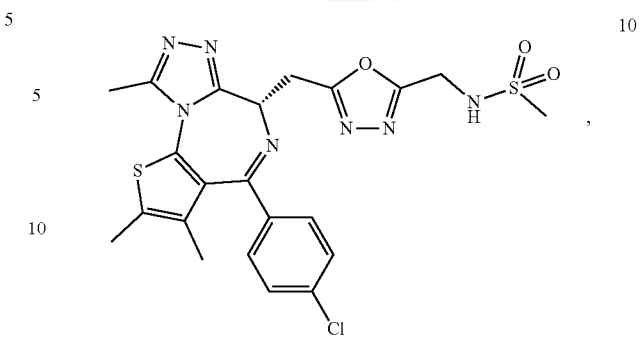
11
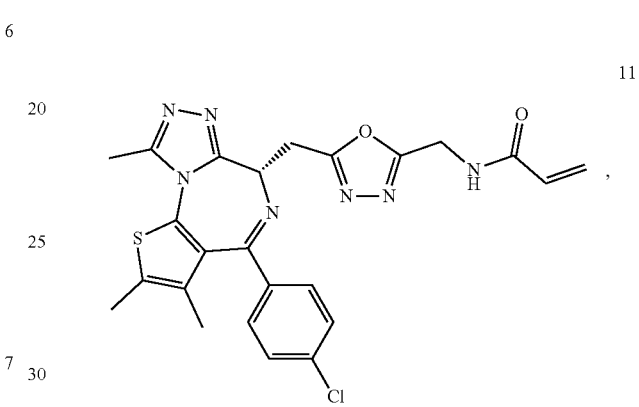
12
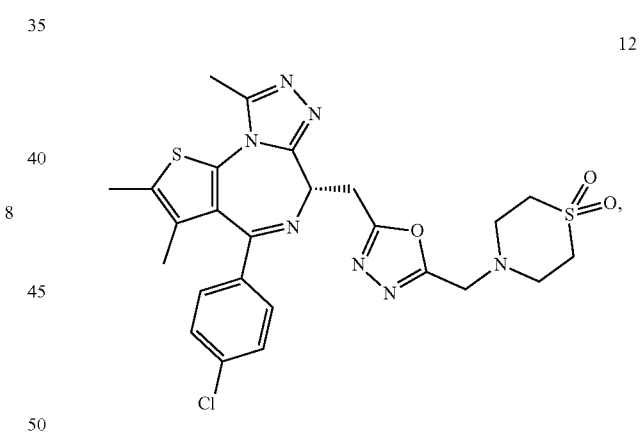
13
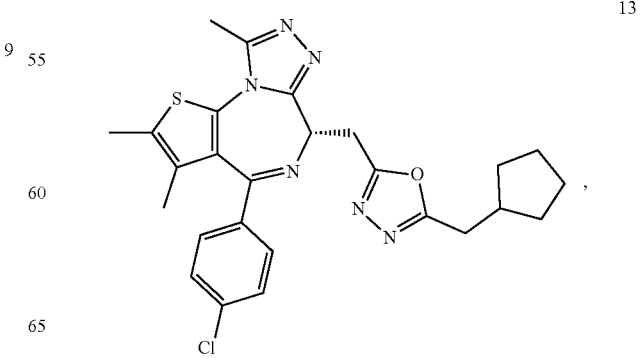

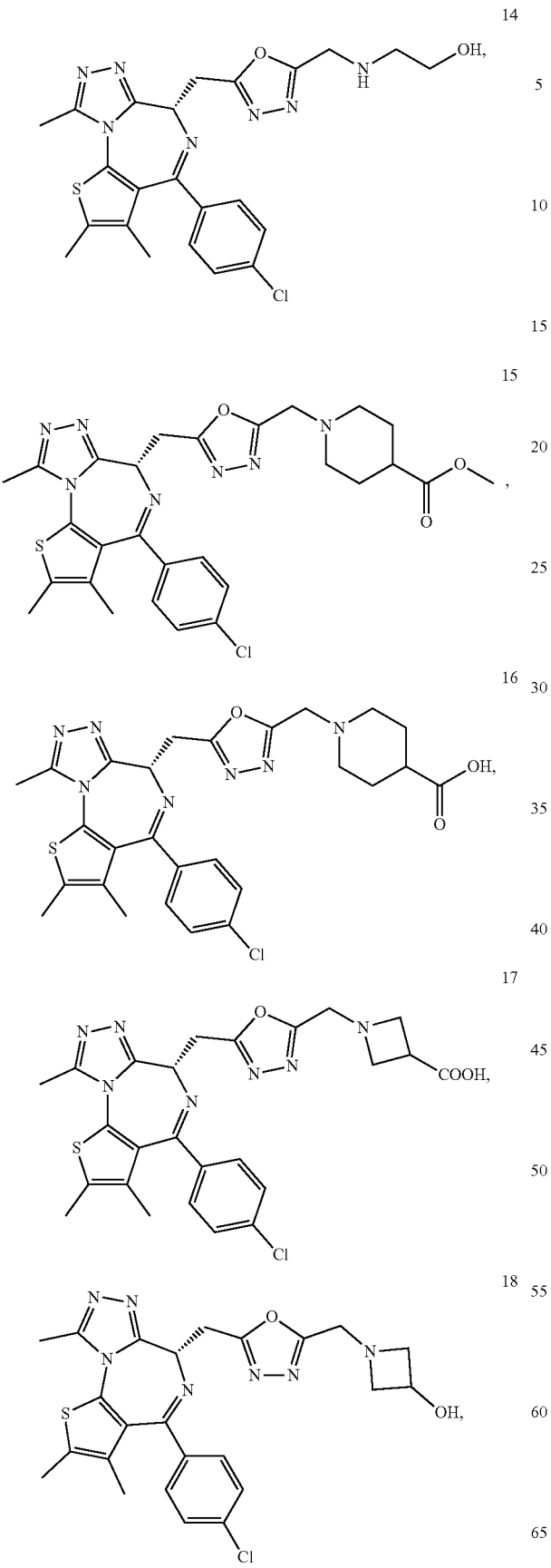
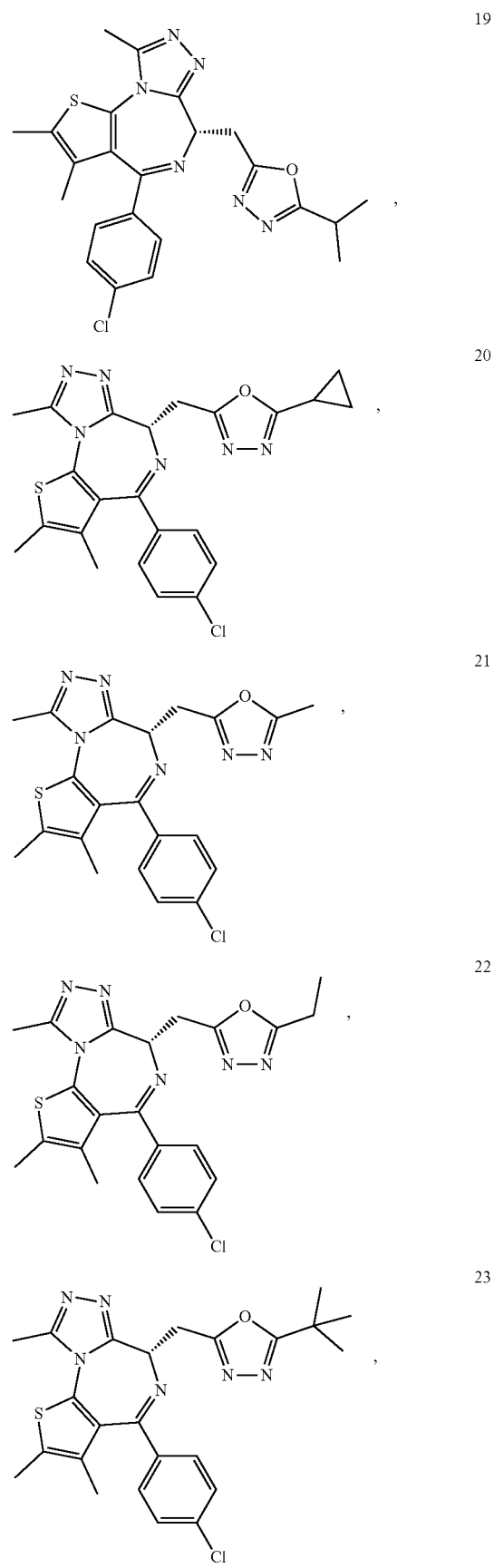

-continued
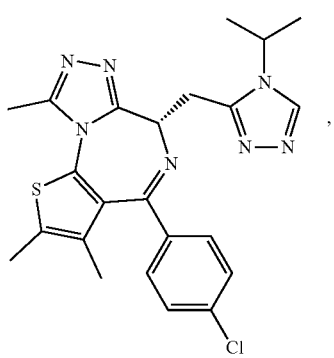
,
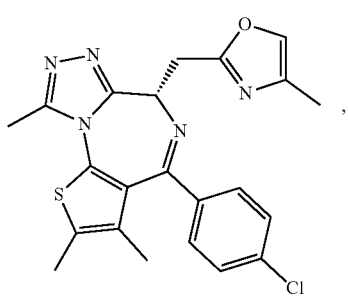
,
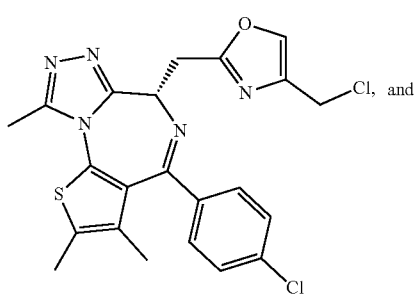
Cl, and
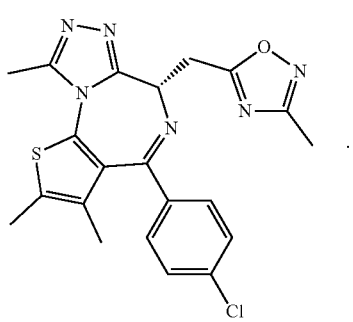
.
14. The method for preparation of compound according to claim 1, comprising one of the following routes:
Scheme 1
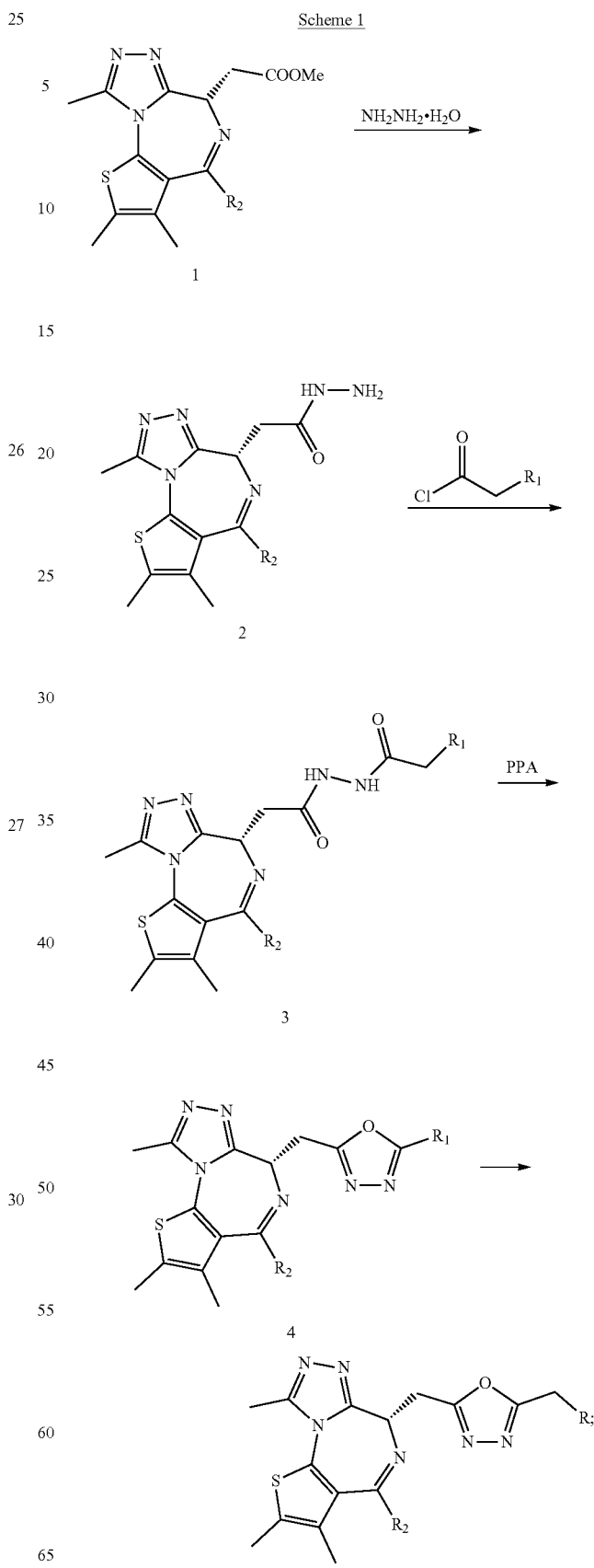

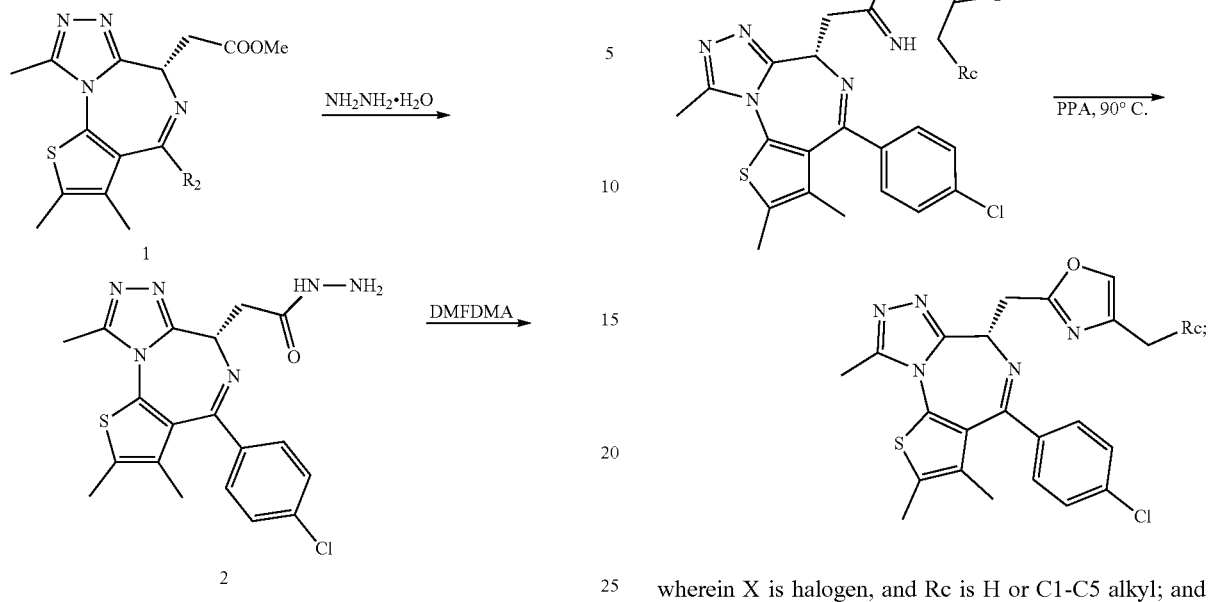
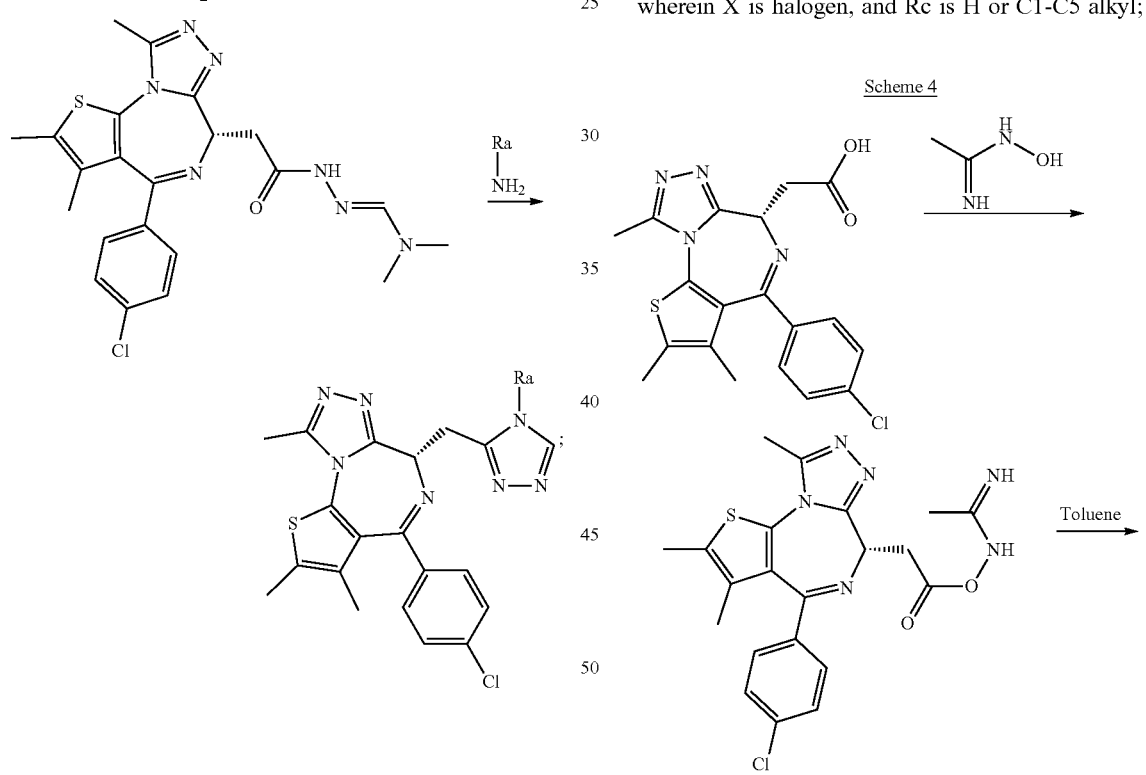
wherein X is halogen, and Rc is H or C1-C5 alkyl; and
Scheme 4
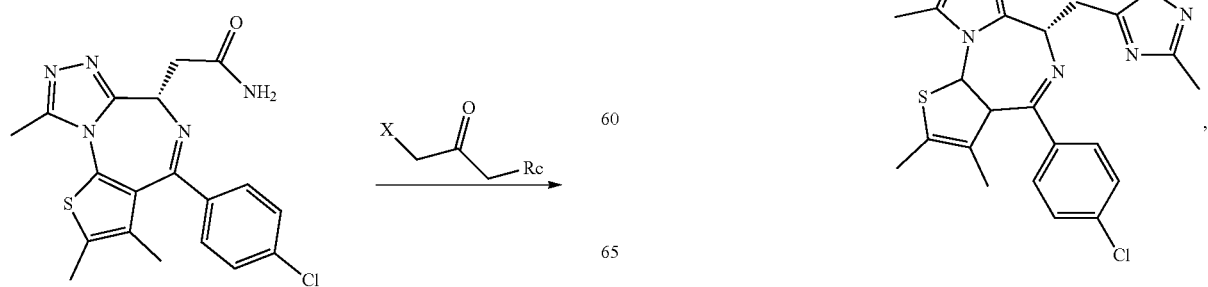

wherein PPA is polyphosphoric acid and DMFDMA is dimethylformamide dimethyl acetal.

15. The drug combination comprising an active ingredient that is the compound or the pharmaceutically acceptable salt thereof according to claim 1 and a pharmaceutically acceptable adjuvant or auxiliary component.

* * * * *